United States Patent [19]

Holtzapple et al.

[11] Patent Number: 5,865,898
[45] Date of Patent: Feb. 2, 1999

[54] METHODS OF BIOMASS PRETREATMENT

[75] Inventors: Mark T. Holtzapple, College Station; Richard R. Davison, Bryan, both of Tex.

[73] Assignee: The Texas A&M University System, College Station, Tex.

[21] Appl. No.: 96,972

[22] Filed: Jul. 27, 1993

Related U.S. Application Data

[63] Continuation-in-part of Ser. No. 926,739, Aug. 6, 1992, abandoned.
[51] Int. Cl.$^6$ ............................ C01F 11/02; C01F 11/06; A23K 1/12
[52] U.S. Cl. ............................ 127/37; 423/165; 426/635; 426/636
[58] Field of Search ........................ 536/56, 124; 162/29, 162/90, 190; 530/500; 426/312, 635, 636; 127/37; 423/165

[56] References Cited

U.S. PATENT DOCUMENTS

| | | |
|---|---|---|
| 3,212,933 | 10/1965 | Hess et al. . |
| 3,639,206 | 2/1972 | Spruill . |
| 3,707,436 | 12/1972 | O'Connor . |
| 3,875,317 | 4/1975 | Ferguson . |
| 3,944,463 | 3/1976 | Samuelson et al. . |
| 4,087,317 | 5/1978 | Roberts . |
| 4,113,553 | 9/1978 | Samuelson . |
| 4,356,196 | 10/1982 | Hultquist . |
| 4,597,830 | 7/1986 | April et al. . |
| 4,842,877 | 6/1989 | Tyson ...................................... 426/271 |
| 5,198,074 | 3/1993 | Villavicencio et al. . |

FOREIGN PATENT DOCUMENTS

| | | |
|---|---|---|
| 8207036 | 10/1983 | Brazil . |
| 0045500 | 2/1982 | European Pat. Off. . |
| 58-98093 | 6/1983 | Japan . |

OTHER PUBLICATIONS

Webster's New Collegiate Dictionary, G.C. Merriam Co., p. 298, 1977.
Millet et al., *Biotechnol. & Bioeng. Symp.* No. 5, pp. 193–219 (1975) Pretreatments to Enhance Chemical, Enzymatic, and Microbiological Attack of Cellulosic Materials.
Winugroho et al.,*Agricultural Wastes* 9 (1984) pp. 87–99 "A Soak–and–Press Method for the Alkali Treatment of Fibrous Crop Residues, Calcium Hydroxide and Sodium Hydroxide Treatments of Rice Straw".
Winugroho M. et al., "A Soak–and–Press Method for the Alkali Treatment of Fibrous Crop Residues", Chemical Abstracts, vol. 100, No. 17, 23 Apr. 1984, abstract No. 137872p, p. 544.
Devendra C., "Chemical Treatment of Rice Straw in Malaysia", Chemical Abstracts, vol. 93, No. 17, 27 Oct. 1980, abstract No. 166609a, p. 539.
Vinod P. Purl, "Effect of Crystallinity and Degree of Polymerization of Cellulose on Enzymatic Saccharification," *Biotechnology and Bioengineering*, vol. XXVI, pp. 1219–1222, (1984).

M. A. Millett et al., "Modifying Wood to Increase Its In Vitro Digestibility," *Journal of Animal Science*, vol. 31, No. 4, pp. 781–788, Oct. 1970.
Wayne E. Moore et al., "Hydrolysis of Wood and Celluose with Cellulytic Enzymes,"*J. Agr. Food Chem.*, vol. 20, No. 6, pp. 1173–1175, (1972).
A. C. Waiss, Jr., "Improving Digestibility of Straws for Ruminant Feed by Aqueous Ammonia," *Journal of Animal Science*, vol. 35, No. 1, pp.
P. J. Morris et al., "Nutritive Value of Ground And/Or Ammoniated Corn Stover," *Can. J. Anim. Sci.*, vol. 60, No. 2, pp. 327–336, (June 1980).
600I Chemical Abstracts, vol. 100, No. 17, Apr. 1984, 137872p, p. 544.
R. W. Mellenberger et al., "Digestion of Aspen, Alkali–Treated Aspen, and Aspen Bark by Goats," *Journal of Animal Science*, vol. 32, No. 4, pp. 756–763, (Apr. 1971).
Harry Schleicher et al., "Changes of Cellulose Accesibililty to Reactions in Alkaline Medium by Activation with Ammonia," *Journal of Polym. Sci., Symp.*, vol. 47, pp. 251–260, (1974).
M. J. Playne, "Increased Digestibility of Bagnese by Pretreatment with Alkalis and Steam Explosion," *Biotechnology and Bioengineering*, vol. XXVI, pp. 426–433 (1984).
A. Felix et al., "In Vitro and In Vivo Digestibility of Soya–Bean Straw Treated with Various Alkalis," *Animal Prod.*, 1990, 51, 47.
John C. Walker et al., "Hydroxides for Treating Crop Residues," *Journal of Animal Science*, vol. 41, pp. 424–425, Abstract 711, (1975).
Fanran Kong et al., "Effects of Cell–Wall Acetate, Xylan Backbone, and Lignin on Enzymatic Hydrolysis of Aspen Wood," *Applied Biochemistry and Biotechnology*, vol. 34/35, pp. 23–35, (1992).
D. Craig Anderson et al., "Chemical Treatment of Ryogenes Straw: In Vitro Dry Matter Digestibility and Compositional Changes," *Journal of Animal Science*, vol. 37, No. 1, pp. 148–152, (1973).

(List continued on next page.)

*Primary Examiner*—Jeffrey C. Mullis
*Attorney, Agent, or Firm*—Baker & Botts, LLP

[57] ABSTRACT

The invention is directed to methods for the pretreatment of a lignocellulose-containing biomass. Pretreatment comprises the addition of calcium hydroxide and water to the biomass to form a mixture, and subjecting the mixture to relatively high temperatures for a period of time sufficient to render the biomass amenable to digestion. The pretreated biomass is digested to produce useful products such as feedstocks, fuels, and compounds including fatty acids, sugars, ketones and alcohols. Alternatively, the pretreatment process includes the addition of an oxidizing agent, selected from the group consisting of oxygen and oxygen-containing gasses, to the mixture under pressure. The invention is also directed to a method for the recovery of calcium from the pretreated biomass.

37 Claims, 10 Drawing Sheets

OTHER PUBLICATIONS

P. H. Robinson et al., "Influence of Ammoniation of High Moisture Barley On Its In Situ Rumen Degradation and Influence on Rumen Fermentation in Dairy Cows," *Can. J. Anim. Sci.*, vol. 68, pp. 839–851, (Sep. 1988).

Harold Tarkow et al., "A Mechanism for Improving the Digestibility of Lignocellulosic Materials with Diluto Alkali and Liquid Ammonia," *ACS*, 95, pp. 197–217, (1969).

Josef Schurz, "How to Make Native Lignocellulosic Materials Accessible to Chemical and Microbial Attack," *Proc. Bioconversion Symp., IIT Delhi*, pp. 37–58, (1977).

W. C. Feist et al., "Alkali Requirements for Improving Digestibility of Hardwoods by Rumen Micro–Organisms," pp. 832–835.

Terry Klopfenstein, "Chemical Treatment of Crop Residues, "*Journal of Animal Science*, vol. 46, No. 3, pp. 841–848, (1978).

F. H. Gharib et al., "In Vitro Evaluation of Chemically–Treated Poplar Bark," *Journal of Animal Science*, vol. 40, No. 4, pp. 734–742, (1975).

K. W. Lin et al., "Effect of Pretreatments and Fermentation on Pore size in Cellulosic Materials," *Biotechnology and Bioengineering*, vol. XXVI, pp. 1427–1433, (1985).

B. S. Capper et al., "Aklali–Treated Roughages for Feeding Ruminants: A Review," *Trop. Sci.*, vol. 19, No. 2, pp. 73–87, (1977).

Iwata "The Simple Method of Straw Disintigration", Nippon Chikusam Gakkai Ho, pp. 189–199 (1930).

Negi et al. "Digestibiltiy of Carbohydrates in Terms of the Conventional Vis a Vis. The Newer Fractions in untreated and Treated Paddy Straw Rations," The India–Veterinary Journal, Nov. 1963, pp. 718–724.

METHODS OF BIOMASS PRETREATMENT

CROSS-REFERENCE TO RELATED APPLICATION

This is a continuation in part of U.S. Ser. No. 07/976,739, filed Aug. 6,1992 now abandoned.

BACKGROUND OF THE INVENTION

1. Field of the Invention

The invention relates to methods for the pretreatment of a lignin containing biomass to render the biomass amenable to digestion. Pretreatment comprises the addition of calcium hydroxide and water to the biomass to form a mixture, and maintaining the mixture at a relatively high temperature. Alternatively, an oxidizing agent, selected from the group consisting of oxygen and oxygen-containing gasses, may be added under pressure to the mixture. The invention also relates to the digested products of the pretreated biomass which includes useful feedstocks, fuels, and chemicals such as sugars, ketones, fatty acids and alcohols, and to a method for the recovery of calcium from the pretreated biomass.

2. Description of the Background

Biomass can be classified in three main categories: sugar-, starch- and cellulose-containing plants. Sugar-containing plants (e.g. sweet sorghum, sugarcane) and starch-containing plants (e.g. corn, rice, wheat, sweet potatoes) are primarily used as food sources. Cellulose-containing plants and waste products (e.g. grasses, wood, bagasse, straws) are the most abundant forms of biomass. Although they are not easily converted to useful products, a well engineered process to convert them to feedstock may potentially be economical since the costs of feedstock are much less than those of sugar- and starch-containing biomass.

Cellulose-containing materials are generally referred to as lignocellulosics because they contain cellulose (40%–60%), hemicellulose (20%–40%) and lignin (10%–25%). Non-woody biomass generally contains less than about 15–b 20% lignin. Cellulose, a glucose polymer, can be hydrolyzed to glucose using acid, enzymes or microbes. Glucose can serve as a feedstock for fuel alcohol and single-cell protein production. Microbial hydrolysis produces cellular biomass (single-cell protein) and metabolic waste products such as organic acids. Acid hydrolysis, although simple, produces many undesirable degradation products. Enzymatic hydrolysis is the cleanest and most preferred approach. However, production of enzymes, mainly cellulase and cellobiase, can be an expensive step. Apart from alcohol production, lignocellulose can be used as inexpensive cattle feed. Since raw lignocellulose cannot be easily digested by cattle, it must be processed to improve its digestibility before it can be fed to ruminants. Also, anaerobic fermentation using rumen microorganisms can produce low molecular weight volatile fatty acids.

Cellulose is the world's most abundant biological material. Approximately 40% to 45% of the dry weight of wood species is cellulose. The degree of polymerization ranges from 500 to 20,000. Cellulose molecules are completely linear, unbranched and have a strong tendency to form inter- and intra-molecular hydrogen bonds. Bundles of cellulose molecules are thus aggregated together to form microfibrils in which highly ordered (crystalline) regions alternate with less ordered (amorphous) regions. Microfibrils make fibrils and finally cellulose fibers. As a consequence of its fibrous structure and strong hydrogen bonds, cellulose has a very high tensile strength and is insoluble in most solvents.

Hemicellulose is the world's second most abundant carbohydrate and comprises about 20% to 30% of wood dry weight. Hemicelluloses, although originally believed to be intermediates in cellulose biosynthesis, are formed through biosynthetic routes different from cellulose. Hemicellulose are heteropolysaccharides and are formed by a variety of monomers. The most common monomers are glucose, galactose and mannose (the hexoses) and xylose and arabinose (the pentoses). Most hemicelluloses have a degree of polymerization of only 200. Hemicelluloses can be classified in three families, xylans, mannans and galactans, named for the backbone polymer.

Lignin is the world's most abundant non-carbohydrate biomaterial. It is a three dimensional macromolecule of enormously high molecular weight. Since its units are extensively cross-linked, it is difficult to define an individual molecule. Lignin provides strength by binding cellulose fibrils together. Being hydrophobic in nature, it prevents water loss from the vascular system and, being highly resistant to enzymatic degradation, it protects plants from insects and microbial attack.

Phenylpropane, an aromatic compound, is the basic structural unit of lignin. The monomers not only cross-link with each other, but also covalently bond to hemicellulose. A great constraint to cellulose and hemicellulose accessibility is the presence of lignin. It has been shown that decreased lignin content causes increased digestibility. Lignin can be removed by physical, chemical, or enzymatic treatments. It must be decomposed to smaller units that can be dissolved out of the cellulose matrix. There are several well developed pulping methods that disintegrate and remove lignin, leaving the cellulose fairly intact. Conventional pulping processes, such as Kraft and sulfite pulping, are too costly as bioconversion pretreatments. Also, economical use of the removed lignin is difficult because its chemical structure and size distribution are highly heterogeneous.

Another major deterrent to enzymatic cellulosic hydrolysis is the highly ordered molecular packing of its crystalline regions. Cellulolytic enzymes readily degrade the more accessible amorphous portions of cellulose, but are unable to attack the less accessible crystalline material. Thus, enzymatic hydrolysis rates increase with decreasing crystallinity index measured by X-ray diffraction methods.

The moisture content of cellulose fibers influences enzymatic degradation. Cellulosic materials are effectively protected from deterioration by enzymes or microbes provided the moisture content is maintained below a critical level characteristic of the material and the organism involved. In general, this critical level is slightly above the fiber saturation point, approximately 40% of dry weight. Moisture plays three major roles: (1) it swells the fibers by hydrating cellulose molecules, thus opening up the fine structure and increasing enzyme access, (2) it provides a diffusion medium for enzymes and for partial degradation products, and (3) it is added to cellulose during hydrolytic cleavage of the glycosidic links of each molecule.

The surface area of lignocellulose is another important factor that determines susceptibility to enzymatic degradation. It is important because contact between enzyme molecules and the cellulose surface is a prerequisite for hydrolysis to proceed. A few other factors that also influence susceptibility include size and diffusibility of enzyme molecules in relation to size and surface properties of capillaries, unit cell dimensions of cellulose molecules, and conformation and steric rigidity of hydro-glucose units.

To enhance susceptibility to enzymatic hydrolysis, lignocellulose pretreatment is an essential requirement. The heterogeneous enzymatic degradation of lignocellulosics is primarily governed by its structural features because (1) cellulose possesses a highly resistant crystalline structure, (2) the lignin surrounding the cellulose forms a physical barrier and (3) the sites available for enzymatic attack are limited. An ideal pretreatment, therefore, would reduce lignin content, with a concomitant reduction in crystallinity and increase in surface area. Pretreatment methods can be classified into physical, chemical, physicochemical, and biological, depending on the mode of action. The literature available on this subject is voluminous. The various pretreatment methods that have been used to increase cellulose digestibility are summarized in Table 1.

TABLE 1

Methods Used for the Pretreatment of Lignocellulosics.

| Physical | Chemical | Physicochemical | Biological |
| --- | --- | --- | --- |
| Ball-milling | Alkali | Steam explosion | Fungi |
| Two-roll milling | Sodium hydroxide | Ammonia Fiber Explosion | |
| Hammer milling | Calcium hydroxide | | |
| Colloid milling | Ammonia | | |
| High pressure | Acid | | |
| steaming | Sulfuric acid | | |
| High energy | Hydrochloric acid | | |
| radiation | Hydrofluoric acid | | |
| Pyrolysis | Gas | | |
| | Chlorine dioxide | | |
| | Nitrogen dioxide | | |
| | Oxidizing agents | | |
| | Hydrogen peroxide | | |
| | Ozone | | |
| | Cellulose solvents | | |
| | Solvent extraction | | |
| | Ethanol-water extraction | | |
| | Benzene-ethanol extraction | | |

Biological Pretreatments

Biological pretreatments employ fungi for microbial de-lignification to make cellulose more accessible. Major biological lignin degraders are the higher fungi, Ascomycetes and Basidiomycetes. Fungal degradation is a slow process and most fungi attack not only lignin, but cellulose also, thus resulting in a mixture of lignin fragments and sugars. Improvements may require developing more specific and efficient microbes.

Physical Pretreatments

Physical pretreatments can be classified in two general categories: mechanical (involving all types of milling) and nonmechanical (involving high-pressure steaming, high energy radiation and pyrolysis). During mechanical pretreatments, physical forces, (e.g. shearing, compressive forces) subdivide lignocellulose into finer particles. These physical forces reduce crystallinity, particle size and degree of polymerization and increase bulk density. These structural changes result in a material more susceptible to acid and enzymatic hydrolysis. However, due to enormously high operating costs associated with the high energy requirements, low yields and large time requirements, these mechanical pretreatments are not practical. Nonmechanical physical pretreatment methods also increase digestibility, but have similar disadvantages and thus are not economical for real processes.

Physicochemical Pretreatments

Steam explosion and Ammonia Fiber Explosion (AFEX) are the main physicochemical pretreatments. Steam explosion heats wetted lignocellulose to high temperatures (about 25° C.) and releases the pressure instantly. Due to rapid decompression, which flashes the water trapped in fibers, physical size reduction occurs. The high temperatures remove acetic acid from hemicellulose, so this process results in some autohydrolysis of the biomass. These changes result in better digestibilities, but the severe conditions also produce degradation products that inhibit hydrolysis and fermentation. These products are removed by washing with water which results in a loss of water soluble hemicellulose. Thus, although digestibilities are improved, biomass degradation and protein denaturization limits the use of steam explosion.

The AFEX pretreatment process soaks lignocellulose in liquid ammonia at high pressure and then explosively releases the pressure. Pretreatment conditions (30° C. –100° C.) are less severe than steam explosion. An increase in accessible surface area coupled with reduced cellulose crystallinity (caused by ammonia contacting) result in increased enzymatic digestibility. However, use of ammonia (a hazardous chemical) and the high pressure release makes the process quite complex and energy intensive.

Chemical Pretreatments

Many chemical treatments have been used for lignin removal and destruction of the lignin crystalline structure. Of these chemicals, acids, gases, oxidizing agents, cellulose solvents, and solvent extraction agents, are all able to increase digestibility, but are not as popular as alkalis. Economics, simpler processes and less degradation favor alkalis as chemical pretreatment agents. However, most of these are process for paper pulping and involves the complete or nearly complete destruction of lignin, and a corresponding destruction of cellulose. Although unimportant in pulping, these pulping process are quite severe and not useful as pretreatments for biomass. Furthermore, the traditional pulping processes used by the paper industry are too expensive as lignocellulose pretreatment methods.

U.S. Pat. No. 4,644,060 to Chou is directed to the use of super-critical ammonia to increase lignocellulose digestibility.

U.S. Pat. Nos. 4,353,713 and 4,448,588 to Cheng are directed to the gasification of biomass or coal which is an endothermic process. These patents also relate to a method for adding the required thermal energy by reacting lime with carbon dioxide which is an exothermic reaction.

U.S. Pat. No. 4,391,671 to Azarniouch is directed to a method for calcining calcium carbonate in a rotary kiln. The reference relates to the paper/pulp industry where the calcium carbonate would be contaminated with waste biomass. The waste biomass is burned to provide the needed heat of reaction.

U.S. Pat. No. 4,356,196 to Hulquist is directed to treating biomass with ammonia.

U.S. Pat. No. 4,227,964 to Kerr is directed to the use of ammonia to promote the kinking of pulp fiber to increase paper strength, not to break down the fibers.

U.S. Pat. No. 4,087,317 to Roberts is directed to the use of lime and mechanical beating to convert pulp into a hydrated gel. There is no mention of lime recovery or enzymatically hydrolyzing the hydrated gel.

U.S. Pat. No. 4,064,276 to Conradsen directed to a process where biomass is covered with a tarp and then ammoniated with ammonia, which is allowed to dissipate into the atmosphere.

U.S. Pat. No. 3,939,286 to Jelks is directed to oxidizing biomass with high-pressure oxygen under elevated temperature and pressure in the presence of an acid catalyst, and a metal catalyst, ferric chloride, to break lignin bonds and to increase digestibility. The catalysts are described as essential to the process and calcium hydroxide is utilized as a neutralizing agent to adjust the resulting pH of the hydrolyzed biomass.

U.S. Pat. No. 3,878,304 to Moore is directed to production of slow-release nonprotein nitrogen in ruminant feeds. An amide, urea, is reacted with waste carbohydrates in the presence of an acid catalyst. The resulting material is pelleted and used as animal feed. Since the nitrogen is released slowly in the rumen, it is nontoxic to the animal.

U.S. Pat. No. 3,944,463 to Samuelson et al. is directed to a process for producing cellulose pulp of high brightness. The cellulose is pretreated with an alkaline compound at a temperature of between about 60° C. to about 200° C. so as to dissolve between 1 and 30% of the dry weight of the material in the pretreatment liquor. The pretreatment liquor preferably contains sodium carbonate, sodium bicarbonate or mixtures thereof, or possible sodium hydroxide.

U.S. Pat. No. 3,639,206 to Spruill is directed to the treatment of waste water effluent derived from a pulping process with calcium oxide or hydroxide to reduce the fiber and color content of the effluent.

U.S. Pat. No. 4,048,341 to Lagerstrom et al. is directed to a process for increasing the feed value of lignocellulosic material by contacting the material with an alkaline liquid, specifically, sodium hydroxide. The alkaline liquid, supplied in excess, is allowed to run off the material before any essential alkalization effect has been reached. After the liquid absorbed in the material has provided its effect, an acid solution is added to the material to neutralize the excess alkali. The reference does not disclose the interrelationship of temperature and time of alkali treatment, nor does it disclose the optimal amounts of the sodium hydroxide and water.

U.S. Pat. No. 4,182,780 to Lagerstrom et al. is directed to a process for increasing the feed value of lignocellulosic materials by alkali treatment and subsequent neutralization of the materials with an acid in a closed system under circulation of the treating agents.

U.S. Pat. No. 4,515,816 to Anthony is directed to a process in which lignocellulose is treated with dilute acid in an amount of about 1.5 to 2.5% of the dry weight of lignocellulose. The mixture is then stored at ambient conditions for 5 to 21 days in an air-free environment.

U.S. Pat. No. 4,842,877 to Tyson is directed to a process for the delignification of non-woody biomass (<20% lignin). In this process, non-woody biomass is treated with a chelating agent, to prevent unnecessary oxidation, and maintained at high pH and high temperatures (150° F. to 315° F.) in the presence of hydrogen peroxide and pressurized oxygen. Hydrogen peroxide is stated to cause a reaction on the cell walls to allow the hemicellulose and lignin to solubilize and be removed through a subsequent hydrolysis process. Oxygen is added to initiate and accelerate the activation of hydrogen peroxide.

The conditions and results of studies reported in the literature using ammonia (gaseous, anhydrous liquid, or $NH_4OH$) and sodium hydroxide as pretreatment agents are listed in Table 2 and Table 3, respectively. The literature available on the use of these two chemicals to enhance lignocellulose digestibility of ruminant feeds, as well as for hydrolysis to glucose, is extensive. The literature on calcium hydroxide pretreatment processes is considerably less compared to that for sodium hydroxide and ammonia. The conditions and results of studies reported in the literature using calcium hydroxide are shown in Table 4.

TABLE 2

Reported Ammoniation Conditions

| Reference | Type of Biomass | Ammonia State | Temp. (°C.) | Time | Pressure | Particle Size | $gNH_3$/kg dry biomass | Effect on Digestibility |
|---|---|---|---|---|---|---|---|---|
| Villareal, 1988 | Coastal Bermuda grass | Gaseous | ambient | — | atmosp. | — | 40 | Increase in DIT, CP[1] |
| Waiss et al., 1972 | Rice straws | $NH_4OH$ | 160 | 1 h | — | 0.64 cm | 26/52 | Increased[2] |
| Waiss et al., 1972 | Rice straws | $NH_4OH$ | ambient | 30 d | atmosp. | 0.64 cm | 50 | Increased[1] |
| Millet et al., 1970 | Aspen sawdust | Liquid | 30/60/90 | 1 h | 155/360/725 psi | — | — | Increased by 51%[2] |
| Millet et al., 1970 | Aspen sawdust | Gaseous | 30 | ½ to 74 h | 155 psi | — | — | Increased by 47%[2] |
| Brown et al., 1987 | Limpo grass | Gaseous | ambient | 30 d | atmosp. | 2.5 cm | 20/30/40 | Increased[1] |
| Kellens et al., 1983 | Wheat straw | $NH_4OH$ | 29 | 21 d | atmosp. | 2 mm | 50 | Increased from 13% to 33%[2] |
| Kellens et al., 1983 | Wheat straw | Gaseous | 6 | 44 d | atmosp. | 2.5 cm | 50 | Increased[1] |
| Hultquist, 1982 | Alfalfa | Liq./Gas. | 20–30 | 30 m | 70–165 psig | 1/16–½ in. | 5/20 | Increased by 50%[2] |
| Millet et al., 1975 | Aspen sawdust | Gaseous | — | 2 h | 70 psi | — | — | Increased by 46%[1] |
| Morris et al., 1980 | Corn stover | — | ambient | — | atmosp. | 1.3 cm | 30 | Increase in DIT, DE[1] |

[1]In vivo.
[2]In vitro.

TABLE 3

Reported NaOH Treatment Conditions

| Reference | Type of Biomass | Temp. (°C.) | Time | Particle Size | g NaOH/100 g solution | g NaOH/100 g biomass | Effect on Digestibility |
|---|---|---|---|---|---|---|---|
| Moore et al., 1972 | Cotton linters | 30 | 1 h | 40 mesh | 1 | 20 | No effect[2] |
| Moore et al., 1972 | Aspen | 30 | 1 h | 40 mesh | 1 | 20 | Increased from 10% to 50%[2] |
| Millet et al., 1970 | Different wood samples | 25 | 1 h | — | 1 | 20 | Increased[2] |
| Fient et al., 1970 | Different wood samples | 25 | 1 h, 2 h | 40 mesh | 0.5, 1 | 2–20 | Increased[2] |
| Baker et al, 197570 | Aspen sawdust | ambient | 2 h | 0.16 cm | 0.5 | 5 | Increased from 41% to 52%[1] |
| Anderson et al., 1973 | Ryegrass straw | ambient | 24 h | 2.54 cm | 0.5–8 | 7.5–120 | Increased from 33% to 90%[2] |
| Mandels et al., 1974 | Bagasse | 72 | 1 h | ⅛" mesh | 2 | — | Increased[2] |
| Mandels et al., 1974 | Newspaper | 70 | 90 m | ⅛" mesh | 2 | 100 | Increased[2] |
| Turner et al., 1990 | Different grass samples | — | 48 m | 4 mm | 3 | — | Increased[2] |

Notation used;
[1]In vivo,
[2]In vitro

TABLE 4

Reported Ca(OH)$_2$ Treatment Conditions

| Reference | Type of Biomass | Temp. (°C.) | Time | Particle Size | g water/g solution | g Ca(OH)$_2$/100 g biomass | Effect on Digestibility |
|---|---|---|---|---|---|---|---|
| Playne, 1984 1972 | Bagasse | 20 | 8 d | 2.25 | 0.87 | 12 to 30 | Increased from 19% to 72%[2] |
| Waller et al., 1975 | Corn cobs | ambient | 14 d | Ground | 0.6 | 4 | Improved digestibility[1] |
| Rounds et al., 1974 | Corn cobs | — | — | — | — | 4 | No effect[2] |
| Gharib et al., 1975 | Poplar bark | ambient | 1 or 150 d | 9.5 mm | 0.6 | 4 to 16 | Increased from 30% to 52%[2] |
| Felix et al., 1990 | Soyabean straw | ambient/frozen | 30 d | Chopped | 0.65 | 2 to 5 | No effect[1] |

Notation used;
[1]In vivo,
[2]In vitro

The references cited in the Tables and below are:
Anderson, D. C.; Ralston, A. T. *J. Anim. Sci.* 1973; 37, 148.
Baker, A. J.; Millett, M. A.; Satter, L. D. *ACS Symposium Series* 1975; 10, 75.
Brown, W. F.; Phillips, J. D.; Jones, D. B. *J. Anim. Sci.* 1987; 64, 1205.
Dawish, A.; Galal, A. G. *In Proc. Conf Anim. Feeds* Trop. Subtrop. Origin 1975.
Felix, A.; Hill, R. A.; Diarra, B. *Anim. Prod.* 1990; 51, 47.
Feist, W. C.; Baker, A. J.; Tarkow, H. *J. Anim. Sci.* 1970; 30, 832.
Gharib, F. H.; Meiske, J. C.; Goodrich, R. D.; El Serafy, A. M. *J. Anim. Sci.* 1975; 40(4), 734.
Hulquist, J. H. U.S. Pat. No. 4,356,296; 1982.
Kellens, R. D.; Herrera-Saldana, R.; Church, D. C. *J. Anim. Sci.* 1983; 56(4), 938.
Mandels, M.; Hontz, J. R.; Kystrom, J. Biotech. Bioeng. 1974; 16, 1471.
Millet, M. A. et al., *J. Anim. Sci.* 1970; 31(4), 781.
Millet, M. A.; Baker, A. J.; Satter, L. D. *In Biotech. Bioeng. Symp.* 1975; 5, 193.
Moore, W. E.; Effland, M. J.; Medeiros, J. E. *J. Agr. Food Chem.* 1972; 20(6), 1173.
Morris, P. J.; Movat, D. N. *Can. J. Anim. Sci.* 1980; 60, 327.
Playne, M. J. Biotech. Bioeng., 1984; 26, 426.
Rounds, W.; Klopfenstein, T. *J. Anim. Sci.* 1974; 39, 251 (abst.).
Turner, N. D.; Schelling, G. T.; Greene, L. W.; Byers, P. M. *J. Prod. Agric.* 1990; 3(1), 83.
Villareal, E. R. Ph.D. Thesis Texas A&M Univ. College Station, TX 1988.
Waiss, A. C. et al., *J. Anim. Sci.* 1972; 35(1). 109.
Waller, J. C.; Klopfenstein, T. *J Anim. Sci.* 1975, 41 424 (abstract).

Playne (1984) investigated the effects of alkali treatment and steam explosion on baggase digestibility. The digestibility of untreated bagasse was 190 g organic matter (OM) /kg bagasse dry matter. It was raised to: 733 g organic matter by using NaOH (and also by using Ca(OH)$_2$ with Na$_2$CO$_3$); to 430 g OM using NH$_3$; and to 724 g OM using Ca(OH)$_2$. When Ca(OH)$_2$ alone was used, a high loading (about 180–300 g Ca(OH)$_2$ kg bagasse) was used. Gharib et al.

(1975) used calcium oxide for in vitro evaluation of chemically treated poplar bark. They reported that calcium oxide increased in vitro true digestibility from 38% to 52% for a 150-day treatment, although little improvement was found for a 1-day treatment. Rounds and Klopfenstein (1974) studied the effects of NaOH, KOH, $NH_4OH$ and $Ca(OH)_2$ on in vivo digestibility of corn cobs by feeding to lambs and on in vitro digestibility using an artificial rumen. $Ca(OH)_2$ alone was unable to increase the in vitro digestibility, although rations treated with $Ca(OH)_2$+NaOH resulted in higher daily gain and feed efficiency for lambs. Waller and Riopfenstein (1975) used various combinations of NaOH, $Ca(OH)_2$ and $NH_4OH$ for treating feed for lambs and heifers and reported that the highest daily gain and lowest feed/gain was obtained for the 3% NaOH +1% $Ca(OH)_2$ rations. Darwish and Galal (1975) used maize cobs treated with 1.5% $Ca(OH)_2$ in a milk production ration and found no significant change in milk output. Felix et al. (1990) evaluated the effects of ensiling and treating soya-bean straw with NAOH, $Ca(OH)_2$ and $NH_4OH$ on ruminant digestibility. Results indicate that there was no significant improvement due to alkali treatment of dry and unensiled straw, although alkali treatment improved digestibility of ensiled straw.

Although the use of calcium hydroxide as a pretreatment agent has been demonstrated, considerably less work has been done employing this chemical compared to other alkalis. Most of the previous work has been performed by animal scientists trying to develop a very simple process to increase the lignocellulose digestibility of animal feed. All these studies were done at room temperature or below, at lower water loadings, for very long periods and without any mixing. These processes required very long treatment times which is very expensive since the reactors must be very large. There is thus a need to improve the currently existing methods of pretreating lignocellulose containing material to render it amenable to enzymatic digestion.

SUMMARY OF THE INVENTION

One embodiment of the invention is directed to an economical process for pretreating a lignocellulose-containing biomass to render the biomass amenable to digestion. Pretreatment comprises adding calcium hydroxide and water to the biomass, and subjecting the biomass to relatively high temperatures for a period of time. The pretreated biomass is digested to produce a useful product.

Another embodiment of the invention is directed to an economical pretreatment method comprising adding calcium hydroxide and water to the biomass to form a mixture, adding an oxidizing agent, selected from the group consisting of oxygen and oxygen-containing gasses, to the mixture under pressure, and subjecting the biomass to relatively high temperatures for a period of time. The pretreated biomass is digested to produce a useful product.

Another embodiment of the invention is directed to a process for recovering calcium from a biomass. After pretreatment, the biomass is carbonated with a carbonating agent to form calcium carbonate. Calcium carbonate is recovered from the pretreated mixture or recovered after digestion and can be reconverted into calcium hydroxide.

DESCRIPTION OF THE INVENTION

Figure 1:
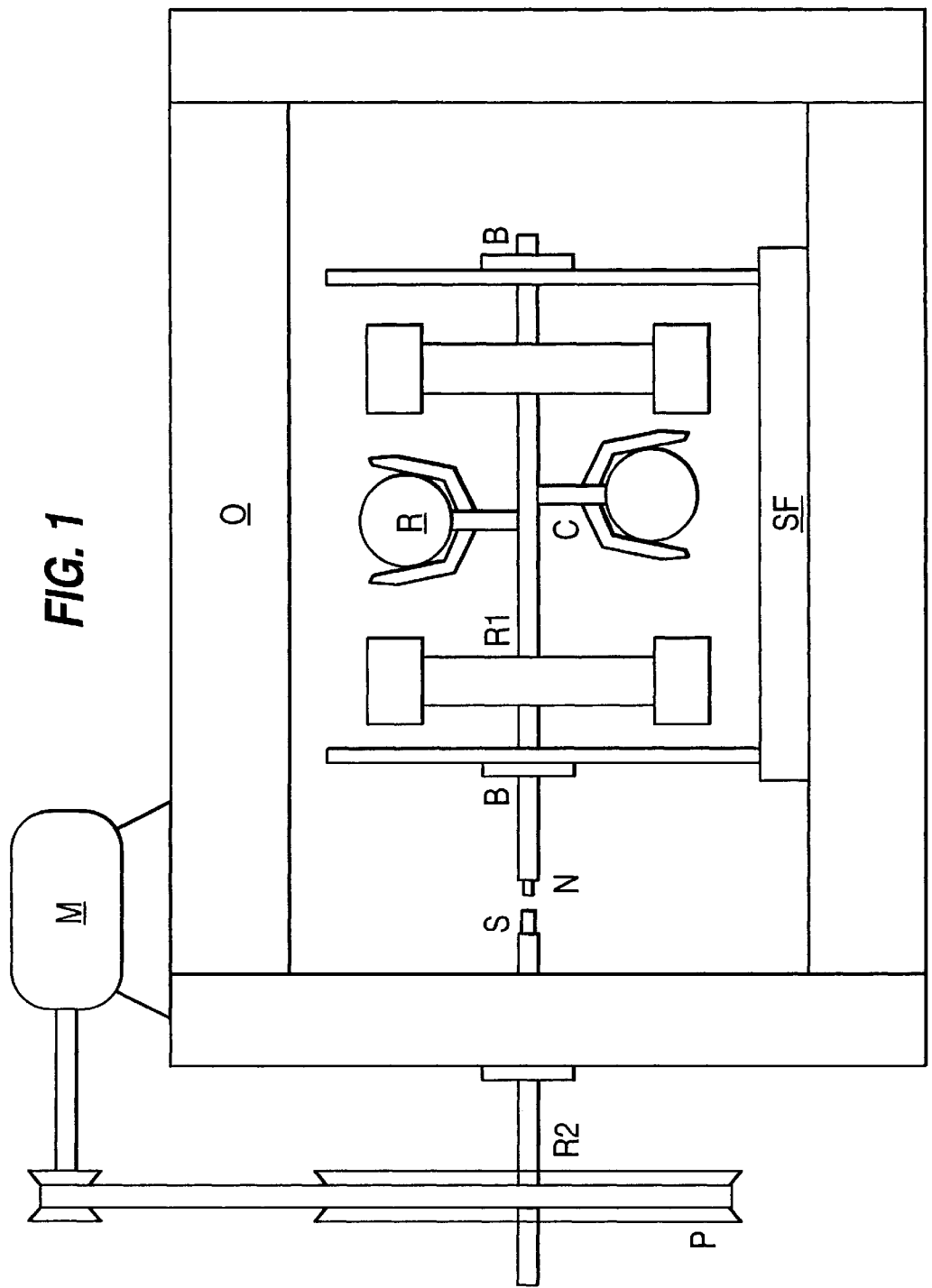
FIG. 1 is a schematic diagram of Reactor System 3.

The present invention comprises economical methods for the pretreatment of a biomass. Pretreatment comprises the addition of calcium hydroxide and water to a biomass to render the biomass susceptible to degradation. Calcium hydroxide is inexpensive and much cheaper than other alkalis. It is safe to handle and, unlike the sodium residue, the calcium residue is little or no problem for animal feed. In an artificial rumen, calcium hydroxide produces calcium acetate which is also safe and nontoxic. Calcium hydroxide $(Ca(OH)_2)$ as the lignocellulose pretreatment agent is therefore very economical. Further, there was also no significant difference in digestibility between $Ca(OH)_2$ pretreated material and $NH_3$ or NaOH pretreated material in animals.

The operating conditions of the pretreatment methods of the invention are a significant improvement over the existing literature. Previous researchers restricted their operating temperature to ambient and below in order to create a very simple process without heaters. These simple processes required extremely long treatment times typically ranging from 8 to 150 days. Raising the treatment temperature could decrease the treatment time, but runs the risk of degrading the lignocellulose. High-temperature treatment conditions have been identified that did not degrade the lignocellulose and resulted in treatment times that were orders of magnitude shorter. The economic impact is significant since the reactor can be orders of magnitude smaller.

Further, previous calcium hydroxide (lime) pretreatment methods used very low water loadings. Since their processes operated at room temperature, good heat transfer was not an issue. They could operate with very little water since the thermal insulating properties of air were not detrimental. However, when operating at a higher temperature, the process benefits by including about ten times more water since its high heat capacity and heat transfer coefficient ensure a uniform temperature. Higher water loadings also provides a medium into which the lime can more uniformly disperse, but are unattainable using conventional procedures. Consequently, most of the previous research in lime treatment used relatively low lime loadings whereas we were able to realistically consider higher loadings can be realistically considered because a lime recovery process is also incorporated into the invention.

In one embodiment, the invention is directed to a method for pretreating a lignocellulose-containing biomass to render the biomass amenable to digestion and comprises providing a lignocellulose-containing biomass, adding calcium hydroxide and water to the biomass to form a mixture, and maintaining the mixture at an elevated temperature and for a period of time sufficient to render the biomass of the mixture amenable to digestion. Types of useful biomass include grass, wood, bagasse, straw, paper, plant material, and combinations thereof. Lignocellulose-containing biomass to which the process of the invention is directed is preferably biomass containing greater than 15% lignin and more preferable biomass containing greater than 20% lignin.

Preferably, biomass to be pretreated is fed into a chipper, grinder, chopper, shredder or the like, to be reduced in size. Resulting biomass chips or particles are preferable about one-half inch or smaller. The biomass particles are then combined with calcium hydroxide and water to form an alkaline biomass mixture. The mixture contains between about 6 to about 19 grams of water per gram of dry biomass and preferably about 16 grams of water per gram of dry biomass. The mixture also contains between about 2 to about 50 grams of calcium hydroxide per 100 grams of dry biomass and preferably contains about 30 grams of calcium hydroxide per 100 grams of dry biomass. Depending on the type of biomass, the preferable amount may be more or less. Calcium hydroxide may be added before or after the water or as an aqueous solution or dispersion.

The aqueous calcium hydroxide/biomass mixture is maintained in reaction chambers, which are preferably stainless steel, at between about 40° C. to about 150° C., preferably between about 100° C. to about 140° C., and more preferably at about 120° C. Depending on the type of biomass, the temperature range may be between about 70° C. to about 110° C., between about 110° C. to about 150° C., or between about 50° C. to about 65° C. The temperature is maintained for between about 1 to about 36, preferably between about 1 to about 20 hours, more preferably about 3 hours. Again, depending on the type of biomass, the time period may be longer or shorter such as between about 15 to about 25 hours.

Another embodiment of the invention is directed to a method for converting a lignocellulose-containing biomass into a useful product and comprises providing a lignocellulose-containing biomass, adding calcium hydroxide and water to the biomass to form a mixture, oxygenating the mixture with pressurized oxygen, maintaining the mixture at an elevated temperature and for a period of time sufficient to render the biomass of the mixture amenable to digestion, and digesting the biomass of the mixture to convert the biomass into the useful product. Oxygen is relatively inexpensive and readily available as pressurized oxygen gas, pressurized air, and other pressurized oxygen-containing gasses. Oxygen is also non-toxin and non-polluting to the environment. Calcium hydroxide is added to a biomass as described above to form a mixture. To the mixture is added an oxidizing agent under pressure selected from the group consisting of oxygen and oxygen-rich gasses. Preferably, the added oxygen-containing gas has a pressure of between about 20 to about 500 psig (pounds per square inch gauge), preferably greater than about 50 psig, and more preferably greater than about 100 psig.

After either of the above-described embodiments, the pretreated biomass is digested by hydrolysis such as acid hydrolysis, enzymatic action, fermentation, or a combination of digestion methods. The digested biomass comprises material which are useful products such as alcohols, acids such as organic acids, sugars, ketones, starches, fatty acids, or combinations thereof. These products can be made into feedstocks such as chemical feedstocks, fuels, and other useful products. Due to the relatively gentle pretreatment conditions, the useful products are obtained in higher quantities and are of a higher quality than products obtained after other pretreatment methods. The maximum amount of material is converted into useful product with as little waste as possible. Further, no toxins or harmful chemicals are introduced into the biomass therefore none need to be removed or even tested for in the final product.

Another embodiment of the invention is directed to a method for recovering calcium from a biomass pretreatment process comprising pretreating the biomass with calcium hydroxide and water to form a mixture, optionally adding an oxidizing agent selected from the group consisting of oxygen and oxygen-containing gasses to the mixture under pressure, and maintaining the mixture at an elevated temperature and for a period of time sufficient to render the biomass of the mixture amenable to digestion, carbonating the mixture or the liquid portion thereof to precipitate calcium carbonate, and recovering the precipitated calcium carbonate. The pH of the carbonated mixture is between about 8.5 and about 10.5, and preferably between about 9.0 and about 10. The calcium carbonate is precipitated in the mixture and can be recovered by filtration, hydroclone separation, sedimentation, centrifugation, or by combinations of these methods. The calcium carbonate may also be heated and converted into carbon dioxide and calcium oxide, and the calcium recovered as calcium oxide.

Alternatively, the pretreated mixture is treated with a carbonating agent, which is preferably carbon dioxide gas which is bubbled into the mixture, forming calcium carbonate. The pretreated and carbonated biomass is digested and the useful product separated from the remaining mixture or residual mixture. The residual mixture, comprising lignin and calcium carbonate, is heated, for example in a kiln, preferably a lime kiln, to convert the calcium carbonate into calcium hydroxide. The heat supplied to the kiln may be derived from the burning of the lignin, making for a highly economical overall process.

The following examples are offered to illustrate embodiments of the invention, but should not be viewed as limiting the scope of the invention.

EXAMPLES

Example 1

Sample Preparation

Raw bagasse was collected from the Animal Science Department of Texas A&M University. For three years, it was lying in the open, covered only by a plastic sheet. Thus, it was first thoroughly washed with water and then dried in an oven (at 80° C.) for about 8 hours. Also, because bagasse deteriorates with storage time, the bagasse used in the present study was more recalcitrant than that used by Holtzapple et al., Appl. Biochem. Biotech. 28/29, 59 (1991). The wheat straw was already clean and did not require washing. Softwood newspaper was the Bryan/College Station, Texas, Eagle newspaper. It was first shredded in a paper shredder. All materials were ground by a Wiley mill to 1×1 mm particle size and then passed through a 40 mesh sieve. Dry weight analysis was done by placing a small sample in an oven, at 80° C. for 24 hr and measuring the weight loss due to water evaporation.

Example 2

Calcium Hydroxide Pretreatment

Calcium hydroxide pretreatment involves reacting biomass with calcium hydroxide in the presence of water at a relatively high temperature. The effectiveness of the pretreatment process was studied for several different reaction conditions. Process variables studied were lime loading (2 to 30 g Ca(OH)$_2$/100 g dry biomass), water loading (6 to 19 g water/g dry biomass), treatment temperature (50° C. to 145° C.) and treatment time (1 hour to 36 hours). The following three types of reactor systems were employed.

Reactor System 1: For initial pretreatment experiments, 500-mL glass Erlemneyer flasks were used as reactors. The flasks were sealed with rubber stoppers and placed in a 100-rpm shaking water-bath. This method was limited to 65° C., the highest temperature attainable by the water bath.

Reactor System 2: Erlenmeyer flasks were placed in an oven, with periodic manual shaking. Only one experiment, at 65° C., was performed by this method. This method resulted in lower yields, thus demonstrating that continuous shaking was required for effective mass transfer.

Reactor System 3: Steel reactors were used for experiments in the 65° C. and 145° C. temperature range. To resist the corrosive nature of calcium hydroxide solutions, the reactors were constructed of 304 stainless steel. The reactors were, 1.5 "I.D.x5"long, cylindrical nipples, with end caps on both ends. To provide mixing inside the reactors, a rotating device was fabricated in the Texas A & M Chemical Engineering Department's machine shop. A schematic diagram of this reactor system is shown in FIG. 1. This device holds the reactors (R) inside the oven (0) and, by rotating them continuously, provides tumble mixing of the contents. It has a steel rod (R1) supported from both ends on two ball bearings (B). The bearings are bolted on a steel frame (SF) that can be placed inside the oven. Six holes are drilled through this rod to hold the clamps (C) that hold the reactors. Set screws hold the clamps in place during rotation. Through the back side of the oven, a 1" hole is drilled. A small rod (R2) supported by a ball bearing (bolted on the oven wall) passes through this hole. A pulley (P) is mounted on the end that is outside the oven. A variable speed AC/DC motor (M) mounted on the top of the oven rotates R2. The steel rc>d that holds the reactors (R1) has a splined end (a small nut (N)) that couples with the pulley (via a socket (S)). This coupling arrangement allow the reactors to be placed in, and removed from, the oven with ease.

To perform the pretreatment experiments, the reactors were prepared by winding at least four layers of Teflon tape on both ends. One end was closed by placing the nipple in a vice and tightening the end cap by a pipe wrench. The reaction mixture was prepared by placing the measured quantities of biomass (7.5 g dry weight) and Ca(OH)$_2$ (according the lime loading) inside the reactors. The material was thoroughly mixed inside the reactors using a spatula. Measured amounts of water were then added to this dry mixed sample. The end cap was placed on the other end of the nipple and tightened. The reactors were then placed in boiling water for 5 to 15 minutes (depending on the pretreatment temperature) to pre-warm them. Prewarming the reactors is necessary to rapidly bring them to higher temperatures. They were then clamped and fixed on the rotating device and placed in the oven maintained at the desired pretreatment temperature. The motor was turned on and the system was left for the desired pretreatment time. After the treatment time elapsed, the reactors were removed from the oven and transferred to a water bath to rapidly lower the temperature to ambient temperature. Samples were them removed from the reactors for hydrolysis. A complete step-by-step procedure is given below.

Optionally, oxygen-containing gas is introduced into the reactor from a high-pressure gas container or tank attached to the system. The gas may be pure pressurized oxygen, compressed air (which is very economical) or any oxygen-containing gas under pressure. The pressure of the oxygen-containing gas can be determined from a pressure gauge ounted on the gas supply container or on the reactor.

Example 3

Calcium Hydroxide Pretreatment—Reactor System 3

1. Remove the old Teflon tape and clean the threads at both ends. Wrap (clockwise) at least four layers of fresh Teflon tape.
2. Label and number all the reactors. 2 or 4 or 6 reactors can be run each time.
3. Close the reactors by placing the cap on one end. Hold the nipple in the vice and tighten the cap using a pipe wrench.
4. Weigh ground and sieved material that has 7.5 g dry weight. Using a funnel, pour it in the labeled reactors.
5. Weigh calcium hydroxide, according to the desired lime loading, and pour into the reactors with the biomass.
6. Using a spatula, mix Ca(OH)$_2$ and biomass thoroughly. This dry mixing is essential to ensure a uniform reaction.
7. Pour water according to desired water loading.
7A. (Optionally) Open a the valve connecting the reactor to a container of oxygen gas under pressure. Close the valve when a specified gauge pressure within the reactor has been achieved.
8. Close the ends of the reactors.
9. Place the reactors in boiling water for about 5 min, for a 50° C. run, to about 15 min, for a 135° C. run. The water boiler takes about 30 min to heat up, so it must be turned on before hand.
10. Heat the oven to the desired pretreatment temperature. The oven takes about 1 hour to reach a stable temperature. Keep the rotating device inside the oven during heating so that it gets prewarmed.
11. Clamp the reactors, making sure that the clamps are in the center of the reactors so that there is no blocking during rotation.
12. Place the clamps in the slots of the rotating rod and tighten the set screws.
13. Place the device in the oven and couple it with the motor using the coupling arrangement.
14. Turn on the motor and keep the rotation speed at the minimum possible. Make sure that the motor does not stall.
15. Observe the temperature of the oven.
16. After the pretreatment time has elapsed, take out the reactors and place them in a cold tap water bath. Let them cool for about 10 min.
17. Perform enzymatic hydrolysis.

Example 4

Filter Paper Assay

The filter paper assay is commonly used to quantitatively study cellulose hydrolysis and measure cellulose activity. Filter paper is used since it is a readily available and reproducible substrate and is neither too susceptible nor too resistant to cellulase enzymes. The filter paper is incubated with various amounts of cellulose enzyme for 1 hour at 50° C. and pH of 4.8. The amount of reducing sugars released in 1 hour is measured by the Dinitrosalicylic Acid (DNS) assay.

(Also see below). The amount of enzyme that produces 2 mg of reducing sugar (expressed as glucose) in 1 hour is equal to 0.185 International Units (1 IU=1 mmole glucose/min).

Figure 2:
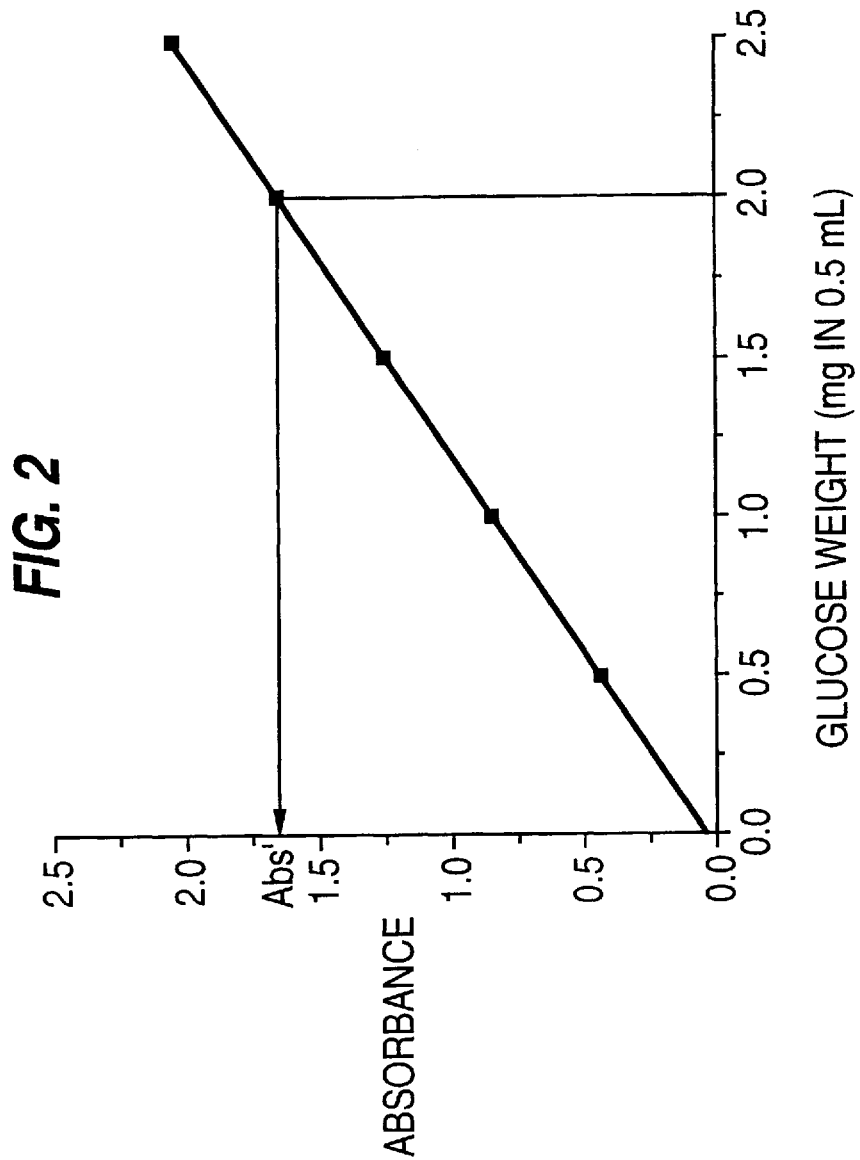
FIG. 2 is a glucose calibration curve for the filter paper assay.

Calibrate DNS reagent using glucose (along with filter paper):

1. Using a 500mg/dl (5mg/mL) glucose standard, prepare 0.5 mL samples in pairs of test tubes according to Table 5.
2. Add 1.0 mL of pH 4.8, 0.05M citrate buffer.
3. Add 1×6 cm filter paper strip (Whitman #1, rolled in a curl). Vortex.
4. Incubate at 50° C. for 1 hour (use capped test tubes). Prevent any shaking
5. Add 3.0 mL of DNS to each test tube.
6. Boil samples for 15 minutes in water bath.
7. Add 10 mL water and vortex.
8. Filter through 0.45 urn nylon membrane filter.
9. Measure the absorbance at 550 nm and prepare a calibration curve of absorbance vs. glucose concentration as shown in FIG. 2.

TABLE 5

Prepare standard solutions for glucose calibration (for filter Paper Assay).

| Glucose Conc. (mg/mL) | Glucose Weight (mg) | Standard (mL) | Distilled Water (mL) |
|---|---|---|---|
| 1.0 | 0.5 | 0.10 | 0.40 |
| 2.0 | 1.0 | 0.20 | 0.30 |
| 3.0 | 1.5 | 0.30 | 0.20 |
| 4.0 | 2.0 | 0.40 | 0.10 |
| 5.0 | 2.5 | 0.50 | 0.00 |

Measure enzyme activity:

1. Add 0, 5, 10, 15, 20 mg enzyme to 10 mL, 0.05M citrate buffer, pH 4.8, and vortex.
2. Pipet 0.5 mL of prepared enzyme samples into pairs of test tubes.
3. Repeat steps 2 to 8 performed during calibration curve preparation.
4. Measure the absorbance at 550 nm.

Measure sugars in the enzyme:

1. Pipet 0.5 mL of 20 mg/mL enzyme sample into pairs of test tubes A.
2. Pipet 0.5 mL of distilled water into pairs of test tubes B.
3. Add 1.0 mL of pH 4.8, 0.05M citrate buffer to test tubes A and B.
4. Repeat steps 5 to 7 performed during calibration curve preparation.
5. Measure absorbance at 550 nm.
6. Calculate absorbance correction factor (ACF) as follows:

$$ACF = \frac{(Abs\,A - Abs\,B)}{(20\text{ mg enzyme}/10\text{ mL}) \times 0.5\text{ mL}}$$

Calculate specific enzyme activity:

1. Using the glucose calibration curve, calculate absorbance, the absorbance for 2 mg glucose weight (see FIG. 2).
2. Apply absorbance correction factor (AC) to absorbance data from the enzyme results.

$Abs_{cor}$=Abs−ACF×E (where E=mg enzyme in 0.5 mL)

Figure 3:
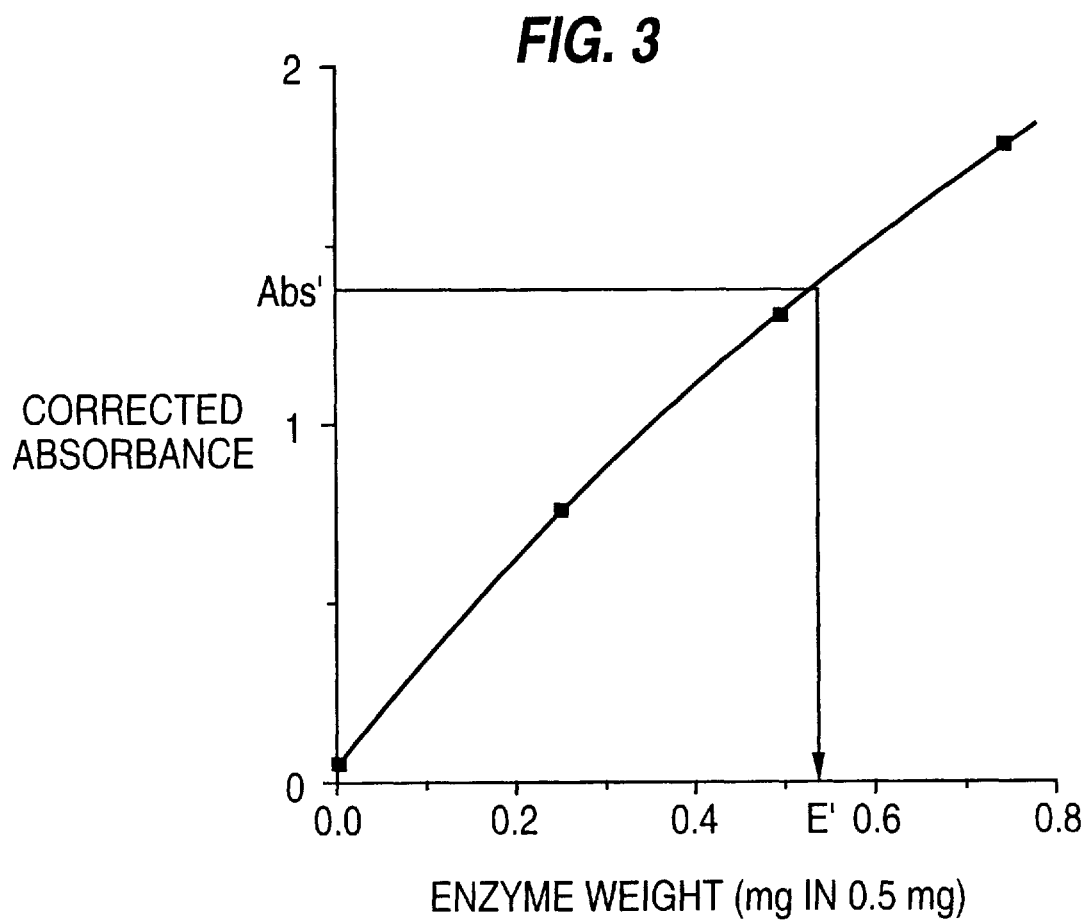
FIG. 3 is an enzyme calibration curve for the filter paper assay.

3. Plot $Abs_{cor}$ vs. E to get FIG. 3.
4. Find E' corresponding to Abs' using FIG. 3.
5. Calculate specific activity:

$$\text{Activity }(IU/mg) = \frac{2\text{ mg glucose}}{E'\text{ mg h}} \times \frac{1\text{ hour}}{60\text{ min}} \times \frac{\text{mmole}}{0.18\text{ mg glucose}}$$

Example 5

Enzymatic Hydrolysis Procedure

The pretreated material (7.5 g dry weight) was transferred from the reactors to 500-mL Erlenmeyer glass flasks. The operating pH and temperature for the enzyme system were kept at 4.8 and 50° C. respectively. The pH was reduced from about 11.5 to 4.8 by adding acetic acid. The total liquid volume was increased to 150 mL by adding distilled water to obtain a 50 g/L slurry of biomass. The required amounts of cellulase and cellobiose we added to the mixture, and the flasks were stoppered and kept in a 100-rpm shaking air bath at 50° C. for 3 days. The enzymatic hydrolysis of control materials was performed using 150 mL of 0.05M, pH 4.8 citrate buffer.

After 3 days, 1 mL liquid samples were withdrawn from each flask using a 1000-mL Eppendorf pipet. The samples were boiled in capped test tubes for 30 minutes to denature the enzyme, thus avoiding further hydrolysis. The boiled samples were filtered through 0.45-um nylon membrane filters. The reducing sugar concentration was measured using the DNS assay (Miller, G. L., Anal. Chem. 1959, 31, 462) with glucose as the calibration standard. Thus, the sugar yields are reported as equivalent glucose/g dry biomass. Both cellulase and cellobiose contain sugars. To measure these sugars, enzymes were added to 150 mL of water in the same concentration as used previously, but without any biomass. One mL samples were taken to measure the sugar concentration. This measured sugar in the enzyme amounts to a correction of 45 mg eq. glucose/g dry biomass that was subtracted from the 3-day reducing sugar yields from the pretreated biomass. The hydrolysis samples were diluted from 13 to 33 times to bring the concentration within the assay range (0.1–1.0 mg/mL).

A detailed hydrolysis procedure is given below:

1. Open one end of the reactors and empty the contents (as much as possible) into the labeled 500-mL Erlenmeyer flasks.
2. To completely transfer the biomass, use water to wash the reactors. Pour this water and biomass mixture into the flasks. Add enough water such that the total liquid volume (water added during the wash+water added during pretreatment) is 140 mL.
3. Add glacial acetic acid to the mixture until the pH reaches 4.8. During acetic acid addition, continuously monitor the pH and stir using a magnetic bar. Note the volume of acetic acid added. If the pH goes below 4.8, use $Ca(OH)_2$ to raise it to 4.8.
4. Add more water to bring the total liquid volume to 150 mL.
5. Add 0.259 g cellulose powder "Cytolase 300 P" (filter paper activity, 215 IU/g powder) and 0.652 mL cellobiose "Novozyme" (activity 250 CBU/mL). Cytolase 300 P was supplied by Genecor, Inc. (South San Francisco, Calif.) and cellobiose was supplied by Novo Laboratories (Wilton, Conn.). The cellulase loading was 7.4 IU/g dry pretreated lignocellulose and the cellobiose loading was 22 CBU/g dry lignocellulose.

6. Place the flasks inside the 100-rpm shaking air bath at 50° C.

17. Close flasks with rubber stoppers after flasks have been warmed for 10 min.

8. Keep flasks in the bath for 3 days.

9. Withdraw 1 mL of sample and boil them for 30 min. in capped test tubes.

10. Filter samples through 0.45 um nylon membrane filter. Perform DNS assay to measure reducing sugars as explained below.

Example 6

Dinitrosalicylic Acid (DNS) Assay

The DNS assay is the most commonly used technique for measuring reducing sugars released by cellulose hydrolysis. A glucose standard is used for the calibration, thus the reducing sugars are measured as "equivalent glucose."

Prepare DNS reagent:

1. Dissolve 10.6 g of 3,5-dinitrosilicylic acid crystals and 19.8 g NaOH in 1416 mL of distilled water.
2. Add 306 g Na-K-tartrate (Rochelle salts).
3. Melt phenol crystals under a fume hood at 50° C. using a water bath. Add 7.6 mL of phenol to above mixture.
4. Add 8.3 g sodium meta-bisulfite.
5. Add NaOH, if required, to the solution obtained to adjust pH to 12.6.

Figure 4:
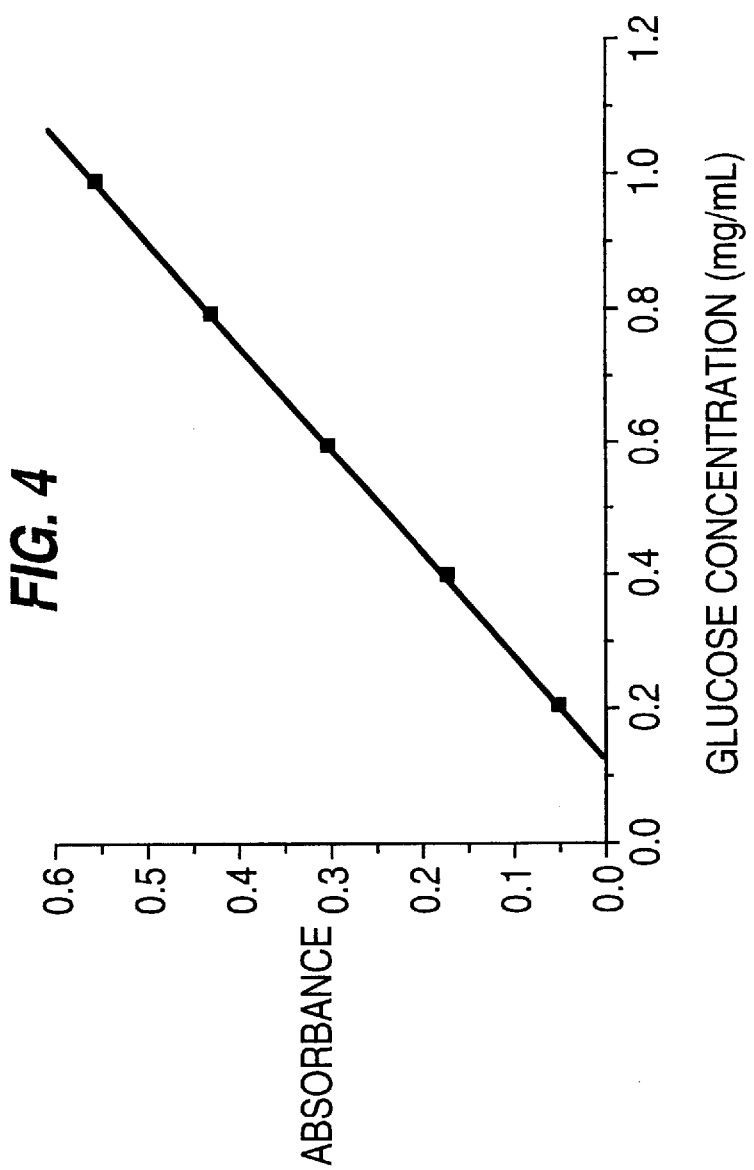
FIG. 4 is a calibration curve for the DNS assay.

Calibrate DNS reagent:

1. Using a 200 mg/dL (2mg/mL) glucose standard, prepare 1 mL samples in pairs of test tubes according to Table 5.
2. Take 0.5 mL of each sample.
3. Dispense 1.5 mL of DNS regent into each test tube using a 5-mL Brinckmann dispensette.
4. Place the caps on the tubes and vortex.
5. Boil samples in a water bath for 15 minutes.
6. Cool the test tubes for a few minutes. Add 8 mL of distilled water and vortex.
7. Zero the spectrophotometer at 550 nm with distilled water (Note: to stabilize the spectrophotometer it should be turned on for at least 1 hour before using).
8. Measure the absorbance.
9. Prepare a calibration curve as shown in FIG. 4.

TABLE 6

Prepare standard solutions for glucose calibration (for DNS Assay.)

| Glucose Concentration (mg/mL) | Standard (mL) | Distilled Water (mL) |
| --- | --- | --- |
| 0.2 | 0.10 | 0.90 |
| 0.4 | 0.20 | 0.80 |
| 0.6 | 0.30 | 0.70 |
| 0.8 | 0.40 | 0.60 |
| 1.0 | 0.50 | 0.50 |

Measure reducing sugars of samples:

1. Dilute the filtered sample into a pair of test tubes such that the sugar concentration lies between 0.1 to 1.0 mg/mL.
2. Vortex the diluted sample.
3. Pipette 0.5 mL of each diluted sample.
4. Dispense 1.5 mL DNS reagent into each test tube.
5. Repeat steps 4 to 8 used in preparation of calibration curve.
6. Calculate sugar concentration from the absorbance of the samples using the calibration curve.
7. Calculate the reducing sugar yield by the following expression:

$$Y = S \times D \times 20$$

Y=reducing sugar yield (mg eq. glucose/g dry biomass)
S=sugar concentration in sample (mg eq. glucose/mL)
D dilution factor
20=150 mL liquid volume/7.5 g dry biomass

Example 7

Calcium Hydroxide Recovery

Two factors motivate recovery of calcium hydroxide from the pretreated biomass. First, an inexpensive recovery and recycle process will reduce the pretreatment costs. Second, high calcium residues have a detrimental effect on its use as cattle feed. Thus, reducing the calcium content results in a more utilizable material. The method for recovering $Ca(OH)_2$ is to wash the pretreated material with water, and to contact or react this wash water containing lime with carbon dioxide. This converts soluble $Ca(OH)_2$ to insoluble $CaCO_3$ that can be removed by precipitation. The $CaCO_3$ can then be heated to produce CaO and $CO_2$. The CaO is hydrated to $Ca(OH)_2$ which can be reused as the lignocellulose treatment agent. Carbon dioxide can, in turn, be reused for lime recovery. Thus, ideally, it is a system capable of total recycling.

The carbonate concentration is quite low when the pH is below 9.5. Thus, to form and precipitate more $CaCO_3$, the pH was maintained above 9.5.

All the recovery experiments were done using bagasse. The experiments to study the recovery process were conducted by two different approaches: Continuous Recovery and Batch Recovery.

1. Continuous Recovery

Figure 5:
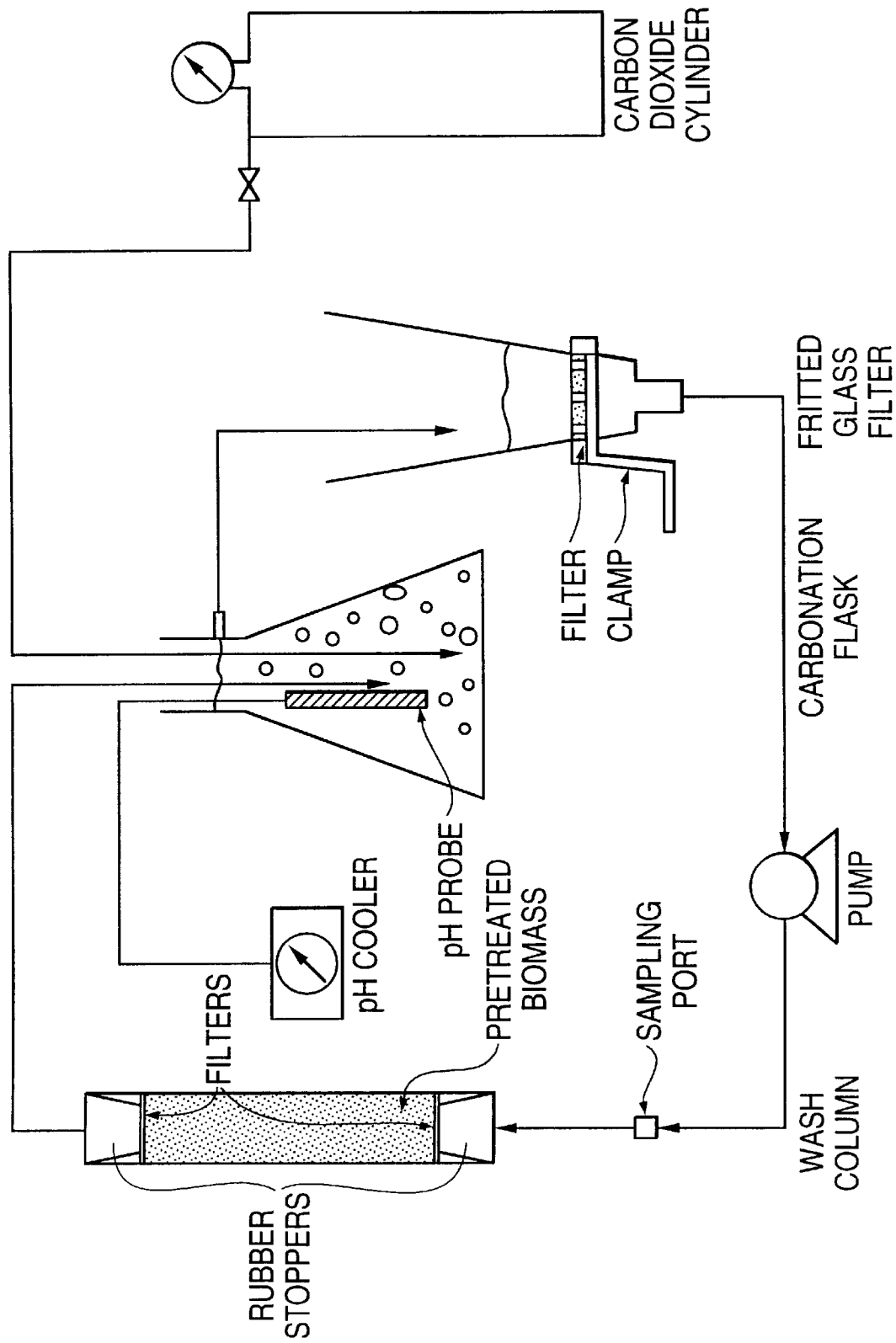
FIG. 5 is a flow diagram for continuous calcium hydroxide recovery.

A systematic flow diagram of the continuous recovery experimental apparatus is shown in FIG. 5. The pretreated bagasse was packed in a 1"I.D.×8.5"high glass column. Rubber stoppers at both ends had connections for the inlet (bottom) and the outlet (top). Filters (nylon cloth) were glued on both stoppers. A peristaltic pump (Watson-Marlow, 502S) pumped water through the column. The average volumetric flow rate was 20 ml/min. The outlet from the column went to a 300-mL flask. Carbon dioxide was bubbled thought the lime-saturated liquid in this flask to produce $CaCO_3$. A pH probe was placed in this flask to continuously monitor the pH. The pH was maintained near 95 by bubbling only as much $C0_2$ as was required to lower the pH from about 12.0 to 9.5. However, because good pH control was lacking, when the pH dropped below 9.5, the required amount of $NH_4OH$ (about 1 or 2 mL) was added to bring the pH back to 9.5. The overflow from the flask went to a filter assembly. Although most of the $CaCO_3$ remained in the flask, filtration was required to remove the $CaCO_3$ present in the overflow. A glass fiber filter (G6, Fisher Scientific, Inc.) was placed between the fritted glass filter and glass jar. A clamp was used to hold it and provide a good seal. The pump suction was the driving force for filtration. The filters were replaced periodically when they clogged with the $CaCO_3$ paste. The filtered water was then pumped back to the column for washing, thus completing the cycle.

The washing was stopped after about one hour. The wash water left in the glass jar clamped to the filter, was transferred to the flask and left for 24 hour to let $CaCO_3$ settle. Clear liquid (1 mL) was taken from the top of the flask. The clear liquid was decanted slowly and collected in another beaker. The bottom portion containing much higher amounts of $CaCO_3$ was discarded after measuring its volume. The same volume of fresh water was added to the system so that the liquid volume before and after precipitation and decantation remained the same. Further recovery of the lime remaining in the biomass was performed with this batch of decanted water for about 45 minutes. After the wash, the $CaCO_3$-saturated water was again left for precipitation and a sample of clear liquid was taken after this second precipitation.

To measure the calcium concentration in the water during washing, 1-mL samples were periodically taken from the column inlet and outlet. The calcium concentration was measured by the atomic absorption apparatus available in the Kinetics Group of the Texas A&M Chemical Engineering Department. Depending on the calcium concentration, the samples were diluted from 11 to 135° C. since the best yields were obtained between 65° C. and 100° C., this wide range ensured that the optimal temperature was found. The pretreatment times of 1 to 36 hours were logical choices since longer times were difficult to justify economically. Since mixing would ensure uniformity of the reaction mixture and probably result in a better pretreatment, continuous shaking was always employed except in one study that used periodic shaking.

In all the experiments, the 3-day reducing sugar yields were used as the measure of enzymatic susceptibility of lime-treated bagasse. The reducing sugar yields were calculated as mg equivalent glucose/g dry bagasse. Typically, 50% and 85% of the 3-day sugars were released in 6 hours and 24 hours, respectively.

Table 7 summarizes the conditions and the reactor systems used in the various bagasse experiments.

and 24 hours was repeated thrice to find the error involved in measuring the 3-day reducing sugar yields. For the 1 hour run, the yields were 112, 125, 111 mg eq. glucose/g dry bagasse, showing a standard deviation of 7.8 mg eq. glucose/g dry bagasse. For the 24 hour run, the yields were 273, 256, 268 mg eq. glucose/g dry bagasse, showing a standard deviation of 8.7 mg eq. glucose/g dry bagasse. These standard deviations can be generalized to apply to the rest of the experiments, and thus other experiments were not repeated.

Example 8

Calcium Acetate Inhibition Experiment

High calcium acetate concentrations are present in the hydrolysis mixture since acetic acid (about 5 mL glacial acetic acid for a sample treated with a lime loading of 30 g $Ca(OH)_2$/100 g dry bagasse) is used to neutralize the lime for pH adjustment. To measure the calcium acetate inhibition of enzymes, and experiment was performed in which group bagasse was ammoniated at the reported optimum conditions. These ammoniation conditions were: temperature=93° C.; treatment time=30 min., water loading=0.25 g water/g dry bagasse, ammonia loading=1.5 g $NH_3$/g dry bagasse, particle size=40 mesh.

Also, there was no explosion (as used in Ammonia Fiber Explosion process) since the pressure was slowly released. This pretreated material was hydrolyzed in enzyme solutions containing various calcium acetate concentrations. The calcium acetate solutions were prepared by adding various amounts of $Ca(OH)_2$ (according to the lime loadings used for the pretreatment) to 150 mL water, and then adding acetic acid to reduce the pH to 4.8. Thus, the calcium acetate concentration in these solutions was the same as for lime-pretreated materials. The enzymes were added to solutions only after the pH was brought to 4.8, thus there was no loss of enzyme acidity due to high pH. The 3-day sugar yield obtained from this ammonia-treated material clearly shows that increased calcium hydroxide loadings decrease sugar

TABLE 7

A summary of conditions used during various bagasse experiments.

| Exp. No. | Reactor System | Temp. (°C.) | Time (h) | Lime Loading (g Ca(OH)$_2$/100 g) | Water Loading (g water/g) | Particle Size |
|---|---|---|---|---|---|---|
| 1 | 1 | 65 | 1, 3, 6, 12, 24, 26 | 30 | 10, 15, 19 | −40 mesh |
| 2 | 2 | 65 | 24 | 30 | 6, 8, 10, 13, 15, 17, 19 | −40 mesh |
| 3 | 3 | 65, 125 | 12, 6 | 30 | 6, 8, 10, 13, 15, 17, 19 | −40 mesh |
| 4 | 3 | 135 | 1, 3, 6, 24 | 10, 20, 30 | 10, 15 | −40 mesh |
| 5 | 3 | 100 | 1, 3, 24 | 10, 20, 30 | 10, 15 | −40 mesh |
| 6 | 1 | 50 | 1, 3, 6, 24 | 2, 5, 10, 15, 20, 30 | 10 | −40 mesh |
| 7 | 3 | 85 | 3, 24 | 5, 10, 15, 20 | 10 | −40 mesh |
| 8 | 3 | 65 | 3, 6, 24 | 5, 10, 15, 20 | 10 | −40 mesh |
| 9 | 3 | 65 | 24 | 10, 15 | 10 | −1 × 1 mm +40 mesh |

The experiment at 50° C. (Bagasse Experiment, Example 2), lime loading=5 g $Ca(OH)_2$/100 g dry bagasse, water loading=10 g water/g dry baggase, and treatment times of 1 yields due to calcium acetate inhibition of the enzyme. For the sample hydrolyzed without addition of $Ca(OH)_2$ to the saccharifictions flask, the sugar yield was 390 mg eq.

glucose/g dry bagasse. This yield is 1.16, 1.14, 1.16, 1.15, 1.25 and 1.22 of that obtained rom samples hydrolyzed in the solutions with 2, 5, 10, 15, 20 and 30 g Ca( )H)$_2$/100 g dry bagasse, respectively. In the subsequent experiments using lime pretreatments, these factors were used to correct the sugar yields. Since this approach is simplified and only approximately corrects for calcium acetate inhibition, the original data (without the correction factor) are reported in addition to the corrected data.

Example 9

Overview of Data (Bagasse)

The 3-day reducing sugar yield for untreated bagasse sample (used as a control) was 40 mg eq. glucose/g dry bagasse which is only about 6% of the theoretical yield. Many different conditions as listed in Table 7 produced high sugar yields. Six high yielding conditions are tabulated in Table 8. The choice of conditions to be used industrially will depend not only on the sugar yields, but also on the expense associated with conditions.

TABLE 8

Conditions resulting in high yields.

| Sample Number | Temp. (°C.) | Time (h) | Calcium Loading (g/100 g) | Water Loading (g/g) | Original Yield (mg/g) | Corrected Yield (mg/g) |
|---|---|---|---|---|---|---|
| 1 | 65 | 24 | 30 | 10 | 597 | 728 |
| 2 | 100 | 24 | 10 | 10 | 580 | 673 |
| 3 | 65 | 24 | 15 | 10 | 555 | 640 |
| 4 | 65 | 24 | 10 | 10 | 533 | 618 |
| 5 | 100 | 1 | 10 | 15 | 525 | 609 |
| 6 | 135 | 1 | 10 | 10 | 517 | 600 |

Example 10

Softwood Newspaper Study

Softwood newspaper is the largest fraction of most residential municipal solid waste. Profitable utilization of softwood newspaper could help solve the ever-growing trash disposal problem. The composition of softwood newspaper is about 70% polysaccharides and 30% lignin, thus, the theoretical yield is bout 750 mg eq. glucose/g dry newspaper. The purpose of this study was to check the feasibility of using Ca(OH)$_2$ to pretreat newspaper. The conditions used for pretreating softwood newspaper are summarized in Table 9.

TABLE 9

Summary of conditions used during various newspaper experiments.

| Experiment Number | Reactor system | Temp. (°C.) | Time (h) | Lime Loading g Ca(OH)$_2$/ 100 g | Water Loading g water/g |
|---|---|---|---|---|---|
| 1 | 3 | 120 | 1, 3, 6, 24 | 30 | 6, 8, 10, 12, 14, 16 |
| 2 | 3 | 60 | 1, 6, 24 | 5, 10, 20, 30 | 10 |
| 3 | 3 | 100 | 24, 3 | 5, 10, 15, 20, 30 | 10, 15 |

Example 11

Overview of Data (Newspaper)

The 3-day reducing sugar yield from an untreated softwood newspaper sample, used as control, was 240 mg eq. glucose/g dry newspaper. Pretreatment processes that work well for many lignocellulosics do not work well for softwood newspaper. This probably results from its high lignin content. The yield improvements with Ca(OH)$_2$ pretreatment found in this present study are comparable to other pretreatments.

Of all the conditions tested, the best yield was obtained for 120° C., 24 hours, 30 g Ca (OH)$_2$/100 g dry newspaper and 16 g water/g dry newspaper. This yield was 344 mg eq. glucose/g dry newspaper (corrected: 430 mg/g). An interesting observation is that the pretreatment works better for either very severe conditions (120° C., 24 hours) or very mild conditions (65° C., 1 hour).

Example 12

Wheat Straw Study

Wheat straw is one of the most abundant agricultural cop residues. In the United States, about 20% of cropland produces wheat, thus large quantities of wheat straw are generated. Typically, based on dry weight, wheat straw is 39% cellulose, 36% hemicellulose, and 10% lignin. According to his composition, the maximum theoretical yield is about 800 mg eq. glucose/g dry wheat straw.

The results for bagasse were used to guide the selection of treatment conditions. The lime loadings were 5, 10, 15 and 20 g Ca(OH)$_2$/100 g dry wheat straw. Only two water loadings were used. Treatment temperatures of 50, 65, 85 and 125° C., and treatment times of 1, 3 and 24 hours, were studied. A summary of the treatment conditions is tabulated in Table 10.

TABLE 10

Summary of conditions used during various wheat straw experiments.

| Experiment Number | Reactor System | Temp. (°C.) | Time (hours) | Lime Loading (g Ca(OH)$_2$/ 100 g) | Water Loading (gH$_2$O/g) |
|---|---|---|---|---|---|
| 1 | 3 | 65 | 3, 24 | 10 | 6, 10, 15, 19 |
| 2 | 3 | 65 | 1, 3 | 5, 10, 15, 20 | 10 |
| 3 | 1 | 50 | 3, 24 | 5, 10, 15, 20 | 10, 15 |
| 4 | 3 | 85 | 1, 3, 24 | 5, 10, 15, 20 | 10 |
| 5 | 3 | 125 | 1, 3, 12, 24 | 5, 10, 15, 20 | 10 |

Example 13

Overview of Data

As in the case of bagasse, several different conditions produced good yields. Since treatment time and temperature play the most important role in process economics, the selection of conditions will not depend strictly on sugar yields. Eight conditions that produced good yields are tabulated in Table 11.

TABLE 11

Conditions resulting in high yields from lime treated wheat straw.

| Sample Number | Temp. (°C.) | Time (hours) | Calcium Loading (g/100 g) | Water Loading (g/g) | Original Yield (mg/g) | Corrected Yield (mg/g) |
|---|---|---|---|---|---|---|
| 1 | 50 | 24 | 10 | 15 | 585 | 679 |
| 2 | 85 | 3 | 10 | 10 | 579 | 672 |
| 3 | 50 | 24 | 20 | 10 | 575 | 667 |
| 4 | 85 | 3 | 20 | 10 | 559 | 698 |
| 5 | 85 | 24 | 20 | 10 | 559 | 698 |
| 6 | 50 | 3 | 10 | 10 | 555 | 639 |

TABLE 11-continued

Conditions resulting in high yields from lime treated wheat straw.

| Sample Number | Temp. (°C.) | Time (hours) | Calcium Loading (g/100 g) | Water Loading (g/g) | Original Yield (mg/g) | Corrected Yield (mg/g) |
|---|---|---|---|---|---|---|
| 7 | 65 | 24 | 10 | 10 | 543 | 630 |
| 8 | 125 | 1 | 10 | 10 | 533 | 618 |

Example 14

Calcium Recovery Study

The best yields for both bagasse and wheat straw were obtained or a lime loading of 10 to 20 g $Ca(OH)_2$/100 g dry material. Thus, an industrial process using such loadings would need significant amounts of lime. A process to recover and recycle lime can reduce the total of lime requirement. Since calcium hydroxide is quite cheap, one main requirement for a recovery process is that it should be simple and inexpensive.

A new recovery process was developed in this invention. $Ca(OH)_2$ was leached or washed out of the pretreated biomass. The lime-saturated wash water was carbonated to convert $Ca(OH)_2$ to insoluble $CaCO_3$ that was subsequently settled. The recovered $CaCO_3$ can be calcinated to form CaO, which can be hydrated to $Ca(OH)_2$, and thus reused. In this study, the washing, carbonation and precipitating steps were performed. The experiments were conducted by two different approaches, namely, continuous and batch recovery processes.

Example 15

Continuous Recovery Process

Three runs were performed to recover $Ca(OH)_2$ from bagasse by the continuous recovery method. The lime treatment conditions used in the continuous lime recovery study are tabulated in Table 12. The recovery results for the corresponding samples are tabulated in Table 13.

TABLE 12

Conditions used for treating bagasse for continuous recovery.

| Sample | Temp. (°C.) | Time (h) | Ca Loading (g/100 g) | Water Loading (g/g) |
|---|---|---|---|---|
| A | 85 | 3 | 10 | 10 |
| B | 85 | 3 | 15 | 10 |
| C | 100 | 1 | 10 | 10 |

TABLE 13

Change in calcium concentration during continuous recovery.

| Sample | Calcium Conc. in Wash Water Initial (ppm) | Final (ppm) | Calcium Conc. in Bagasse g/100 g Initial (ppm) | Final (ppm) |
|---|---|---|---|---|
| A | 1075 | 33 | 5.4 | 2.1 |
| B | 1392 | 10 | 8.1 | 2.3 |
| C | 947 | 19 | 5.4 | 2.0 |

The calcium content in the raw bagasse sample was 0.4 g Ca/100 g dry bagasse. The residual calcium content in the bagasse sample was brought down to about 2 g Ca/100 g dry bagasse from 5.4 g Ca/100 g dry bagasse (Samples A and C) and to 2.3 g Ca/100 g dry bagasse from 8.1 g Ca/100 g dry bagasse (Sample B). This shows that 68% of the added calcium was removed from Samples A and C and 75% of added calcium was removed from Sample B. The reduction in a content showed that the recovery process is working fairly well. However, if the pretreated lignocellulosics are to be used as cattle feed, this residual calcium concentration might be slightly high (1 to 2 g Ca/100 g dry biomass is desired).

One of the main drawbacks observed with the continuous recovery experiment was that there was some channeling inside the bagasse-filled column. Thus, the wash water was not contacting all of pretreated material. This definitely would lower the process effectiveness. With the use of some packing material and an efficient column design, it might be possible to increase the continuous recovery process efficiency. However, this invention used a second approach (i.e. batch recovery) that provides good contact by mixing the wash water and biomass.

Example 16

Batch Recovery Process

In this experiment, instead of packing the pretreated material in a column, a glass beaker was used to mix the biomass with wash water. This wash water was saturated with $CaCO_3$ and had a pH of 8.7. The lime-saturated wash water obtained after filtration was contacted with $CO_2$ and the resulting $CaCO_3$-containing solution was allowed to settle. The pretreatment conditions and the corresponding calcium contents are given in Table 14 and Table 15, respectively.

TABLE 14

Conditions used for treating bagasse for batch recovery.

| Sample | Temp. (°C.) | Time (h) | Ca Loading (g/100 g) | Water Loading (g/g) |
|---|---|---|---|---|
| D, E | 65 | 24 | 10 | 10 |
| F, G, H, I, J, K | 65 | 24 | 15 | 10 |

TABLE 15

Change in calcium concentration during batch recovery.

| Sample | Number of Washings | ($gNH_4OH$/100 g) Wash Water | Calcium Conc. in Wash (ppm) Initial | (ppm) Final | Calcium Conc. in Bagasse (ppm) Initial | (ppm) Final |
|---|---|---|---|---|---|---|
| D | 6 | 0 | 955 | 7 | 5.4 | 1.7 |
| E | 6 | 0 | 892 | 16 | 5.4 | 1.7 |
| F | 6 | 0 | 1109 | 14 | 8.1 | 2.2 |
| G | 10 | 0 | 1192 | 13 | 8.1 | 1.5 |
| H | 10 | 0.2 | 1154 | 6 | 8.1 | 1.5 |
| I | 10 | 0.4 | 1056 | 6 | 8.1 | 1.4 |
| J | 10 | 1.6 | 1306 | 12 | 8.1 | 1.6 |
| K | 10 | 8.7 | 1070 | 4 | 8.1 | 1.7 |
| Untreated | 10 | 0 | 988 | 8 | 8.1 | 1.3 |

The first three samples (D, E, and F) used six washings whereas the other samples used ten washings. For a lime loading of 10 g $Ca(OH)_2$/100 g dry bagasse (Samples D and E), with six washings, the calcium concentration was reduced to about 1.7 g Ca/100 g dry bagasse, and for a lime loading of 15 g Ca(OH)2/100 g dry bagasse (sample P) with six washings, the calcium concentration was reduced to about 2.2 g Ca/100 g dry bagasse. Thus about 75% of added calcium was removed.

Sample F and G received the same lime treatment. Whereas sample F was washed six times Sample G received four additional washings. These additional washings reduced the residual calcium content from 2.2 to 1.5 g Ca/100 g dry bagasse. Thus ten washings were able to remove 86% of the added calcium.

Since it is possible that the calcium atoms are chemically bound to the cellulose and other macromolecules of bagasse, simple washing with water may not work beyond a certain limit. To explore the possibility that bound calcium ions (+2), could be replaced by NH4+ions, the lime-treated bagasse was washed with an ammonium hydroxide solution. The ammonium hydroxide concentration varied from 0.2 to 8.7 g $NH_4OH$/100 g water. The $KH_4OH$ was a 30% (w/w) solution of ammonia in water.

These experiments shoved that the ammoniated wash water was not able to further recover calcium.

In all the previous samples, ammonia was added to the carbonated water to adjust the pH to 9.5. This ensured that the carbonate ions dominated, thus enhancing the precipitation of $CaCO_3$. For Samples R and I, samples for calcium analysis were drawn from settled wash water that was carbonated to pH 6.7, and also from settled carbonated wash water that has been raised to pH 9.5 by adding ammonia. It was found that it was essential to have the pH about 9.5 in order to effectively recover the $CaCO_3$. Although this experiment used ammonia to adjust the pH to 9.5, industrially this would be achieved by having a good control on the $CO_2$ addition. After lime treatment, the pH is about 11.5. Only the amount of $CO_2$ needed to reduce the pH to 9.5 would be added.

All the recovery experiments show that except for lime loading, the other pretreatment conditions (i.e. treatment time, temperature and water loading) do not affect the recovery process. To determine if there are pretreatment reactions that hinder the recovery process, lime was recovered from untreated material, i.e. a physical mixture of bagasse and $Ca(OH)_2$. The calcium concentration in the wash water had a pattern similar to the other samples. The residual calcium content was 1.3 g Ca/100 g dry bagasse which is the lowest obtained from all the recovery experiments. Thus, there seems to be greater calcium binding to the biomass resulting from pretreatment process. However, the effect is small since ten washings of pretreated material had residuals of about 1.5 to 1.7 g Ca/100 g dry bagasse. Thus, there is not much difference in the recovery process for the pretreated material and for the untreated material.

An important question is how far can one atmosphere $CO_2$ lower the pH. *Trichoderma reesei* cellulase operates at pH 4.8. The pH of pretreated biomass is about 11.5, so an acid must be added to lower the pH. During alcohol fermentation processes, much $CO_2$ is generated, so it will be the cheapest acid for pH adjustment. To answer this question, a simple experiment was performed in which a few lime-saturated wash water samples were bubbled with 1 atmosphere $CO_2$ for about 15 min. The minimum pH that was reached was about 6.5. Thus a stronger acid than $CO_2$ will be required to lover the pH to 4.8. It would be more desirable to use a cellulase system that operates at pH 7 such as those in bacteria (e.g. *Clostridium thermocellum*).

Thus it is seen that calcium hydroxide is an excellent pretreatment agent. Many different conditions produced high sugar yields. There was no significant effect of water loading on sugar yields, although 10 g water/g dry material produced slightly higher yields. Lime loadings of 10 and 15 g $Ca(OH)_2$/100 g dry material worked well. It was generally found that the lover temperatures (50° C., 65° C.) required longer times (24 hours), whereas higher temperatures (135° C.) needed shorter times (1 hour) to produce high yields.

The recovery process was able to reduce the calcium content in biomass from 8.1 to about 1.5 g Ca/100 g dry material, thus recovering 86% of the added calcium.

Example 17

Circulation Methods

Figure 6:
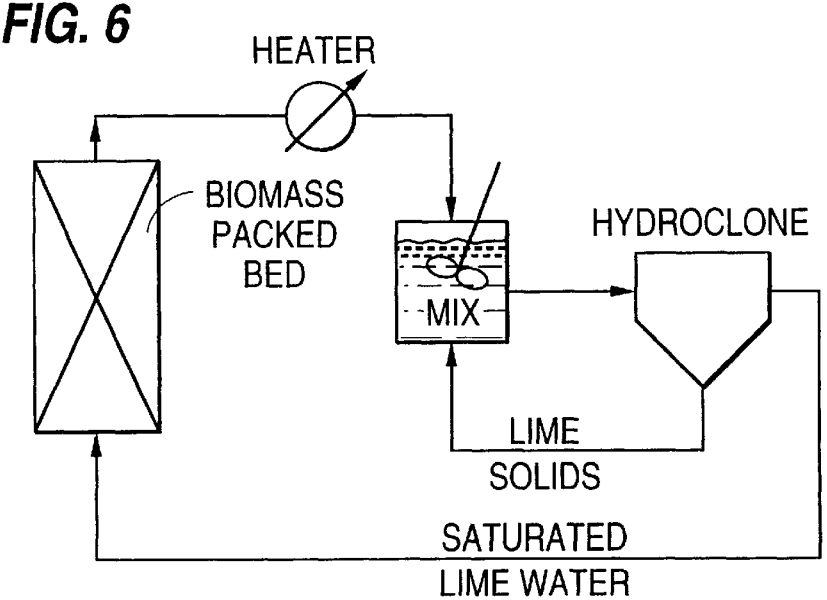
FIG. 6 is a techematic diagram of one embodiment of using a hydroclone to separate lime solids from lime solution.

To prevent the addition of excess lime, the biomass may be contacted with a solution of hot lime water. This may be accomplished in a number of ways:

Method 1: A solution of hot (temperature range of from about 40° C. to about 150° C.) saturated lime water is circulated through a packed bed of biomass for a time period of from about 1 hour to about 36 hours. As the solution exits the bed, it is heated to replace heat loss in the packed bed. The solution of saturated lime water can be prepared by mixing excess lime with water and separating the excess solid lime from the water phase by filtration, hydroclone separation (FIG. 6), settlement, or centrifugation.

Figure 7:
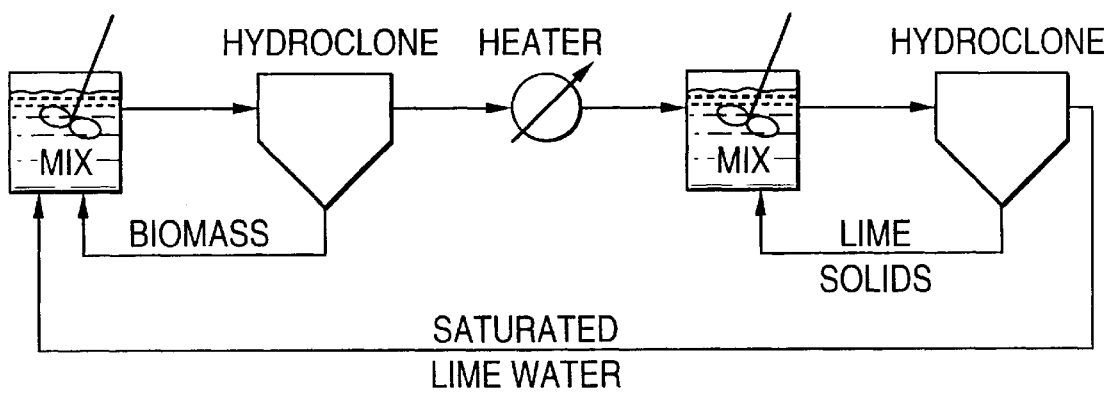
FIG. 7 is a schematic diagram of another embodiment of using a hydroclone to separate lime solids from lime solution.

Method 2: A solution of hot (temperature range of from about 40° C. to about 150° C.), saturated lime water is circulated through a stirred slurry of biomass for a time period of from about 1 hour to about 36 hours. The biomass is separated from the solution by a filter, hydroclone (FIG. 7), settler, or centrifuge. As the solution exits the hydroclone, it is heated to replace heat loss in the stirred slurry of biomass. The solution of saturated lime water can be prepared by mixing excess lime with water and separating the excess solid lime from the water phase by filtration, hydroclone separation (FIG. 7), settlement, or centrifugation.

In either Method 1 or Method 2, the lime solids must always be kept in contact with hot water at the highest temperature in the loop, such as between 40° C. and 150° C. This is required because lime is relatively more soluble in cold water than in hot water. if the water contacting the lime solids were cold, it would dissolve too much lime. Then, if the lime solution were heated later, lime would either precipitate out and foul the heat exchanger or deposit on the biomass. This explains why the water is heated before it contacts lime solids rather than after.

Example 18

Different Permutations

Figure 8:
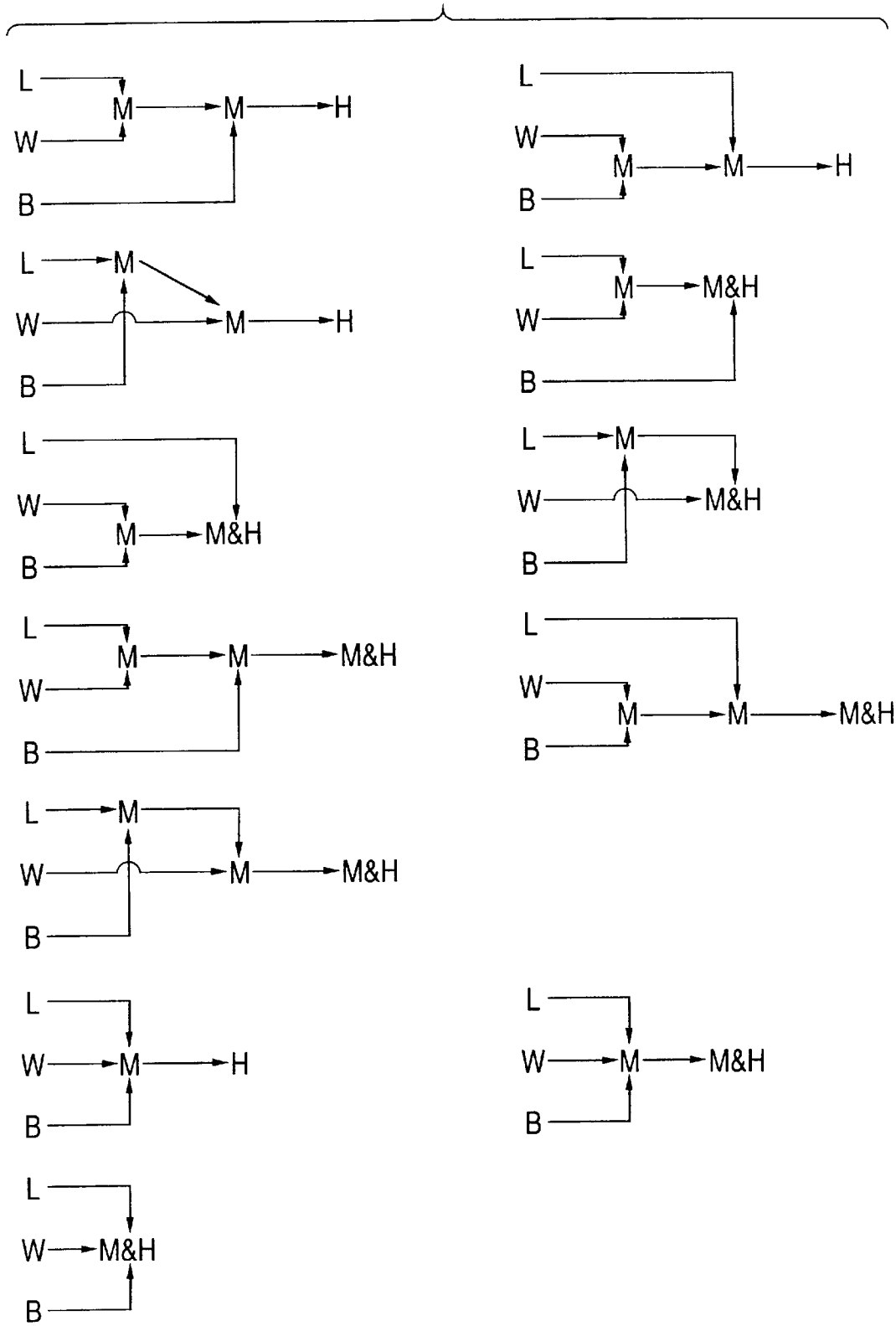
FIG. 8 is a schematic diagram showing different possible permutations of pretreating biomass with lime.

The materials needed for this invention include: Biomass, lime, or calcium hydroxide, and water. The manipulative procedures for this invention include: Mixing, heating, and simultaneous mixing and heating. Thus, these materials and procedures are capable of a number of permutations, as diagrammatically shown in FIG. 8. The notations used in FIG. 8 are: L—lime; W—water; B—biomass; M—mixing; H—heating; and M & H—simultaneous mixing and heating. An arrow in FIG. 8 signifies adding, introducing, or a step to be performed.

Example 19

Lime Treatment Process for Ruminant Animal Feed Production

Figure 9:
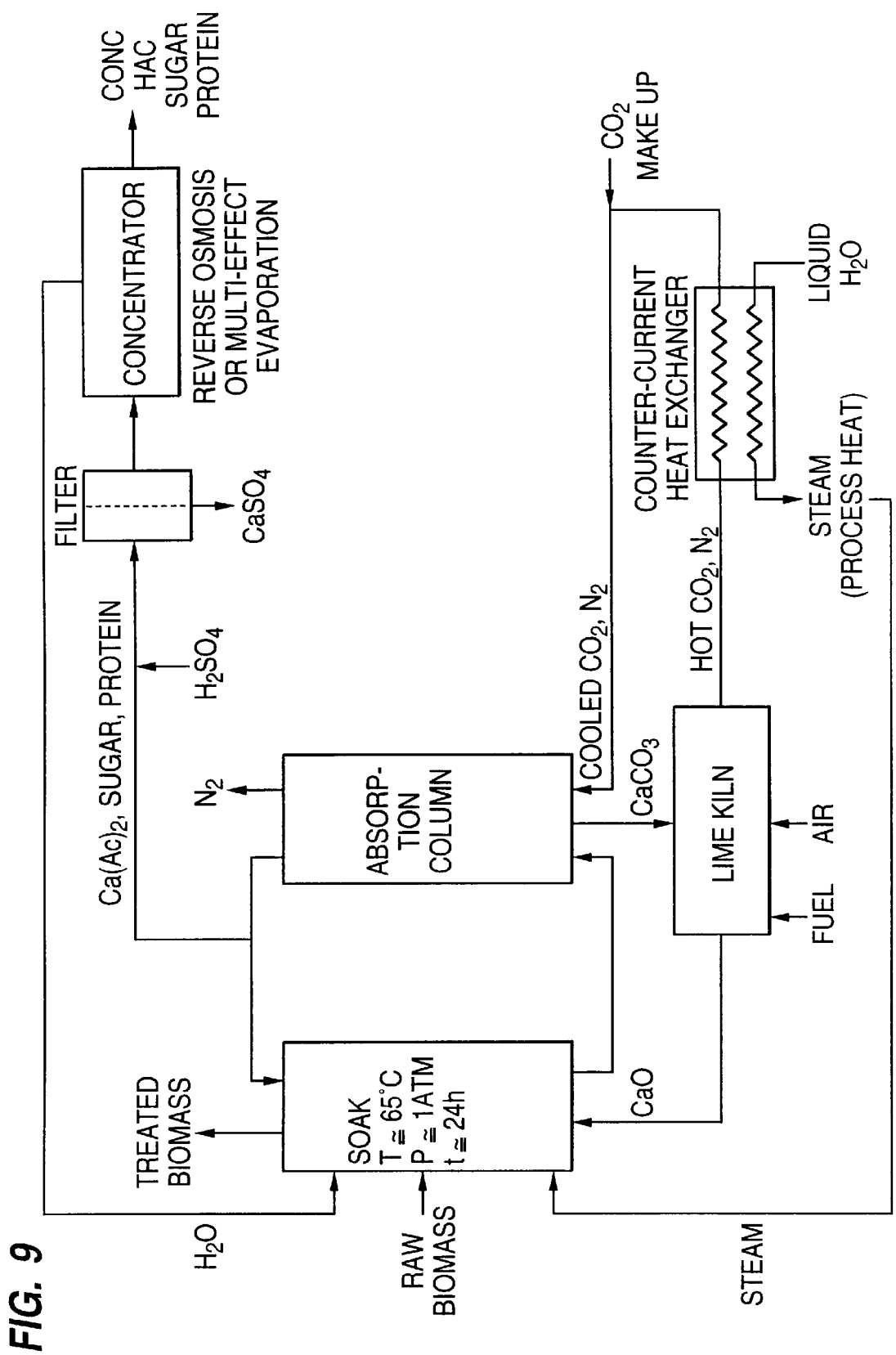
FIG. 9 shows the lime treatment process for ruminant animal feed production.

FIG. 9 shows the lime treatment process for ruminant animal feed production. The lime may be added directly to the biomass, as shown. Alternatively, the biomass may be contacted with a circulating solution of saturated lime water to avoid excess lime addition. Regardless of the addition method, the raw biomass is soaked in hot (ca. 65° C.) lime water for about 24 hours. Then, after the reaction is complete, the lime water is circulated through an adsorption column where it is contacted with carbon dioxide. The carbon dioxide reacts with the lime to form insoluble calcium carbonate which is filtered out and sent to a lime kiln. The calcium carbonate is heated to about 1200° C. in the lime kiln which drives off the carbon dioxide. The hot exit gases (primarily carbon dioxide with some nitrogen from the combustion air) are cooled in a countercurrent beat exchanger recovering high-pressure steam that may be used for electricity production and/or process heat. The cooled carbon dioxide is recycled to the absorption column where the carbon dioxide again reacts with lime water. Inert, such as nitrogen, will exit the absorption column. Make-up carbon dioxide must be added to replace any losses.

The circulating lime water will contain free sugars and protein extracted from the biomass. In addition, there will be some calcium acetate produced from the acetyl groups on the hemicellulose. A bleed stream will be taken off from the circulating loop that will be acidified with sulfuric acid so the calcium ions are precipitated as gypsum. The free sugars, protein, and acetic acid (HAc) will be concentrated by an appropriate technology (e.g reverse osmosis or multi-effect evaporation). It may be sold as monogastric (e.g. chickens, pigs) animal feed.

The treated biomass will emerge from the process in a wet state. If the ruminant animals are located close to the processing plant, they may eat it directly in the wet state. If it must be stored for awhile before it is consumed, it may be dried in the steam driers we have previously described in past disclosures.

Example 20

Pretreatments with Calcium Hydroxide and Pressurized Oxygen

Figure 10:
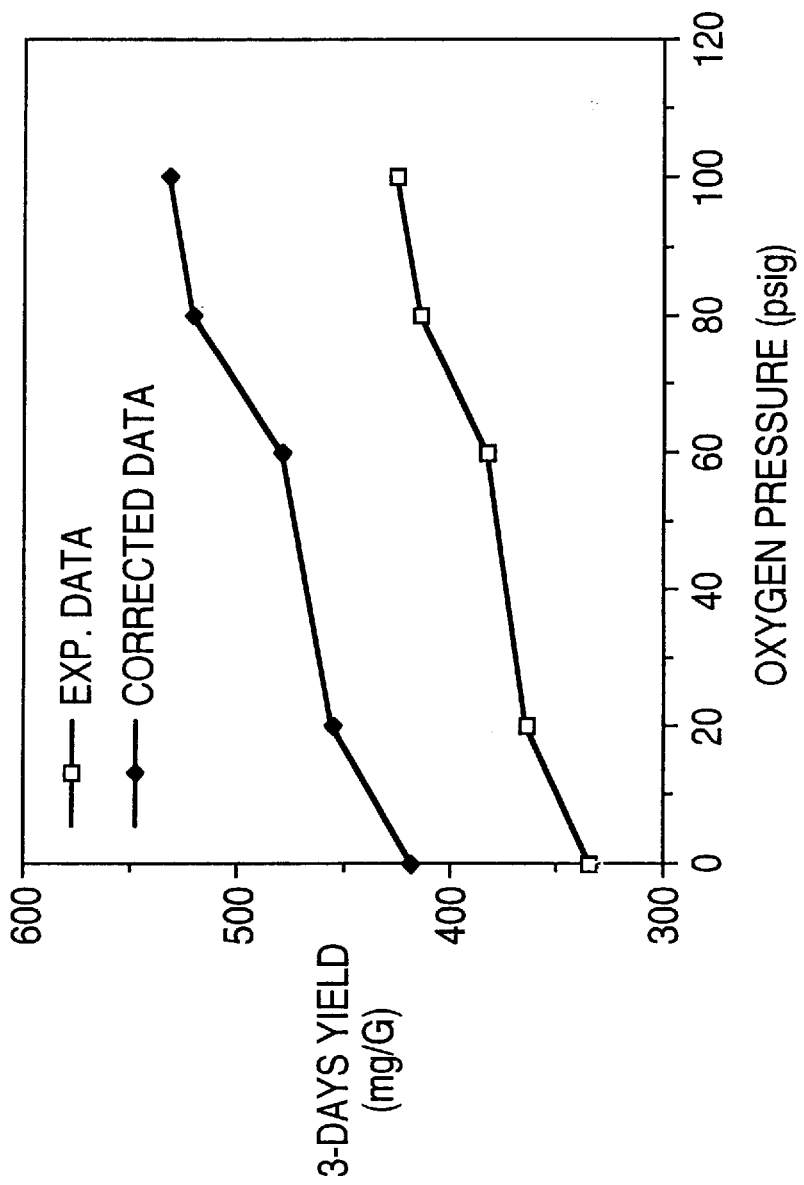
FIG. 10 is a graph of oxygen pressure verses yield to show the effect of oxygen on the hydrolysis of newspaper.

Oxygen is believed to partially oxidizes the lignin which opens the biomass structure making it more enzymatically digestible. Oxygen from high-pressure oxygen tanks was added to samples of newspaper under increasing pressure (FIG. 10). Treatment conditions were consistent with those previously described. Temperature of the biomass was 120° C. for 24 hours with 30 g calcium hydroxide/100 g dry newspaper, and water at 16 g/g dry newspaper. Increasing amounts of oxygen-containing gas was introduced to samples of newspaper from high-pressure tanks. After pretreatment, samples were digested enzymatically and the yield of glucose determined after three days. Newspaper treated with only lime resulted in a yield of 418 mg eq. glucose/g dry newspaper. For comparison purposes, untreated raw newspaper yields 240 mg eq. glucose/g dry newspaper. With 20 pounds/square inch gauge (psig), glucose yield increased over 10%. With increasing oxygen pressure up to 100 psig, glucose yield increased to over 500 mg eq.

Useful oxygen pressures are between about 20 psig to about 500 psig and preferable are between about 100 to about 400 psig. Oxygen is supplied to the biomass from high-pressure sources such as pure oxygen gas, oxygen-containing gas, or compressed air.

Figure 11:
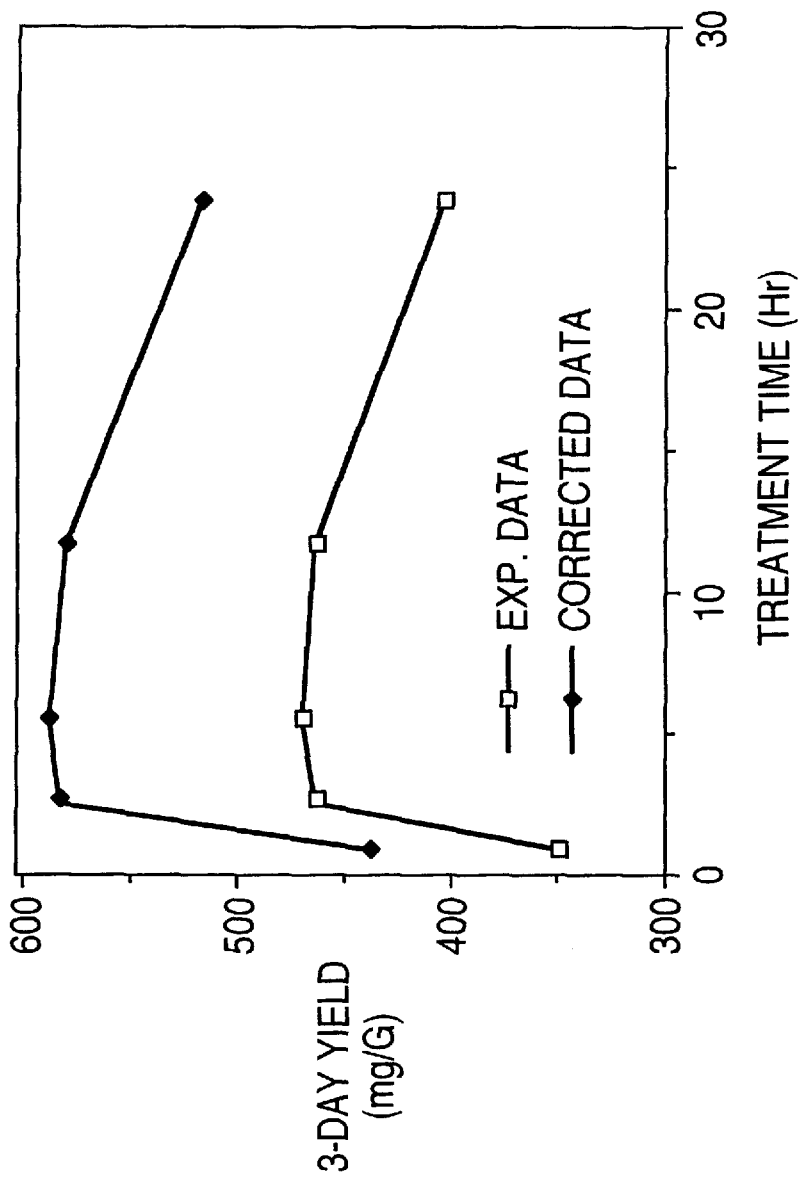
FIG. 11 is a graph of pretreatment time verses yield to show the effect of treatment time on the hydrolysis of newspaper.

In a second series of experiments (FIG. 11), samples of newspaper were pretreated with lime at 30 g/100 g dry newspaper, water at 6 g/g dry newspaper, and oxygen at 100 psig. These sample were pretreated for up to 24 hours. The pretreated samples were enzymatically digested and the sugar content determined. Maximal yield with oxygen pressures of 100 psig was observed at three hours of pretreatment—580 mg eq. of glucose/g of dry newspaper.

Other embodiments and uses of the invention will be apparent to those skilled in the art from consideration of the specification and practice of the invention disclosed therein. It is intended that the specification and examples be considered exemplary only, with the true scope and spirit of the invention being indicated by the following claims.

We claim:

1. A method for pretreating a lignocellulose-containing biomass comprising the steps of adding calcium oxide or hydroxide and water and an oxidizing agent to the biomass to form a mixture; and pretreating the biomass for oxidizing lignin without degrading the lignocellulose by maintaining the mixture at greater than ambient temperature, but less than 100° C. for a period of less than about 36 hours, so that the pretreated biomass contains a weight of glucose that is susceptible to hydrolysis that is greater than about 75% by weight of the total glucose present in the biomass before pretreatment.

2. The method of claim 1 wherein the lignocellulose-containing biomass contains greater than 20% lignin.

3. The method of claim 1 wherein the oxidizing agent is added to the mixture at a pressure of between about 20 to about 500 psig.

4. The method of claim 1 wherein the oxidizing agent is added to the mixture at a pressure of about 100 psig.

5. The method of claim 1 wherein the mixture contains between about 6 to about 19 grams of water per gram of dry biomass.

6. The method of claim 1 wherein the mixture contains about 16 grams of water per gram of dry biomass.

7. The method of claim 1 wherein the mixture contains between about 2 to about 30 grams of calcium oxide or hydroxide per 100 grams of dry biomass.

8. The method of claim 1 wherein the mixture contains about 30 grams of calcium hydroxide per 100 grams of dry biomass.

9. The method of claim 1 wherein the lignocellulose-containing biomass is selected from the group consisting of grass, wood, bagasse, straw, paper, plant material, and combinations thereof.

10. The method of claim 1 wherein the mixture is maintained elevated between about 40° C. to about 150° C.

11. The method of claim 1 wherein the mixture is maintained elevated between about 100° C. and about 140° C.

12. The method of claim 1 wherein the mixture is maintained elevated about 120° C.

13. The method of claim 1 wherein the period of time is between about 1 and about 36 hours.

14. The method of claim 1 wherein the period of time is about 3 hours.

15. The method of claim 1 wherein the elevated temperature is about 120° C., the period of time is about 3 hours, and the oxidizing agent pressure is about 100 psig.

16. The method of claim 1 wherein the weight of glucose that is susceptible to hydrolysis is greater than about 90% by weight of the total glucose present in the biomass before pretreatment.

17. The method of claim 1 wherein the glucose rendered susceptible to hydrolysis comprises cellulose and hemicellulose.

18. The method of claim 1 wherein pretreatment does not degrade said biomass.

19. The method of claim 1 wherein the mixture is dry mixed before pretreatment.

20. The method of claim 1 wherein the mixture is continuously mixed during pretreatment.

21. A method for pretreating a lignocellulose-containing biomass comprising the steps of adding calcium oxide or hydroxide and water and an oxidizing agent, selected from the group consisting of oxygen and oxygen-containing gasses, to the biomass to form a mixture; pretreating the biomass for oxidizing lignin without degrading the lignocellulose by maintaining the mixture at greater than ambient temperature, but less than 100° C. for a period of less than about 36 hours, so that the pretreated biomass contains a weight of glucose that is susceptible to hydrolysis that is greater than about 75% by weight of the total glucose present in the biomass before pretreatment; and hydrolyzing the pretreated biomass.

22. The method of claim 21 wherein the pretreated biomass is hydrolyzed by acid hydrolysis, enzymatic action, fermentation or a combination thereof.

23. The method of claim 16 wherein the weight of glucose that is susceptible to hydrolysis is greater than about 90% by weight of the total glucose present in the biomass before pretreatment.

24. The method of claim 21 wherein the glucose rendered susceptible to hydrolysis comprises cellulose and hemicellulose.

25. The method of claim 21 wherein pretreatment does not degrade said biomass.

26. A method for recovering calcium from a biomass pretreatment process comprising:
   a) pretreating the biomass for oxidizing lignin without degrading the lignocellulose by adding calcium oxide or hydroxide and water and an oxidizing agent to the biomass to form a mixture and maintaining the mixture at greater than ambient temperature, but less than 100° C. for a period of less than about 36 hours, so that the pretreated biomass contains a weight of glucose that is susceptible to hydrolysis that is greater than about 75% by weight of the total glucose present in the biomass before pretreatment;
   b) carbonating the pretreated mixture or a liquid portion thereof to precipitate calcium carbonate or bicarbonate; and
   c) recovering the precipitated calcium carbonate or bicarbonate.

27. The method of claim 26 wherein the pH of the carbonated mixture is between about 8.5 and about 10.5.

28. The method of claim 26 wherein the pH of the carbonated mixture is between about 9.0 and about 10.

29. The method of claim 26 further comprising heating the carbonated mixture to form carbon dioxide and calcium oxide, and recovering the calcium oxide.

30. The method of claim 26 wherein the precipitated calcium carbonate or bicarbonate is recovered by filtration, hydroclone separation, sedimentation, centrifugation or a combination thereof.

31. The method of claim 26 wherein the mixture is dry mixed before pretreatment.

32. The method of claim 26 wherein the mixture is continuously mixed during pretreatment.

33. A method for recovering calcium from a biomass pretreatment process comprising:
   a) pretreating the biomass for oxidizing lignin without degrading the lignocellulose by adding calcium oxide or hydroxide and water and an oxidizing agent, selected from the group consisting of oxygen and oxygen-containing gasses, to the biomass to form a mixture and maintaining the mixture at greater than ambient temperature, but less than 100° C. for a period of less than about 36 hours, so that the pretreated biomass contains a weight of glucose that is susceptible to hydrolysis that is greater than about 75% by weight of the total glucose present in the biomass before pretreatment;
   b) adding a carbonating agent to the pretreated mixture or a liquid portion thereof to form calcium carbonate or bicarbonate;
   c) heating the calcium carbonate or bicarbonate to form calcium oxide;
   and recovering the calcium oxide.

34. The method of claim 33 wherein the carbonating agent is carbon dioxide gas.

35. The method of claim 33 wherein heating is performed by burning the remaining lignin of the digested biomass.

36. The method of claim 33 further comprising the step of digesting the carbonated mixture.

37. The method of claim 36 wherein digestion is performed by acid hydrolysis, enzymatic action, fermentation or a combination thereof.

* * * * *